US012051321B2

(12) United States Patent  
Sugiyama

(10) Patent No.: US 12,051,321 B2  
(45) Date of Patent: Jul. 30, 2024

(54) CONTROL METHOD, CONTROL DEVICE, AND RECORDING MEDIUM

(71) Applicant: Panasonic Intellectual Property Management Co., Ltd., Osaka (JP)

(72) Inventor: Masashi Sugiyama, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 184 days.

(21) Appl. No.: 17/632,729

(22) PCT Filed: Dec. 10, 2020

(86) PCT No.: PCT/JP2020/046128  
§ 371 (c)(1),  
(2) Date: Feb. 3, 2022

(87) PCT Pub. No.: WO2021/171737  
PCT Pub. Date: Sep. 2, 2021

(65) Prior Publication Data  
US 2022/0277626 A1  Sep. 1, 2022

(30) Foreign Application Priority Data  
Feb. 27, 2020  (JP) ................................ 2020-031221

(51) Int. Cl.  
*G16H 20/00* (2018.01)  
*G08B 7/06* (2006.01)

(52) U.S. Cl.  
CPC ............... *G08B 7/06* (2013.01); *G16H 20/00* (2018.01)

(58) Field of Classification Search  
CPC .......... G08B 7/06; G16H 20/00; G16H 50/20; G06F 9/505  
See application file for complete search history.

(56) References Cited

U.S. PATENT DOCUMENTS 7,164,345 B2 * 1/2007 Park ...................... H02J 7/0044  
340/309.7  
7,558,158 B2 * 7/2009 Wang ...................... G04G 13/02  
368/10  
(Continued)

FOREIGN PATENT DOCUMENTS

EP  2 323 003 A2  5/2011  
JP  2004-013848 A  1/2004  
(Continued)

OTHER PUBLICATIONS

International Search Report and Written Opinion issued on Mar. 16, 2021 in International Patent Application No. PCT/JP2020/046128; with English translation.

*Primary Examiner* — Nay Tun  
(74) *Attorney, Agent, or Firm* — Rimon P.C.

(57) ABSTRACT

A control method executed by a computer to control a device that outputs a stimulus to a user includes: obtaining a stimulus start time that is a time when the device is to start outputting the stimulus; determining whether or not the stimulus start time obtained satisfies a predetermined condition; generating a pattern extended or contracted in a time direction from an initial pattern indicating a timewise change in an intensity of the stimulus when the stimulus start time obtained is determined to satisfy the predetermined condition; and controlling the device to start outputting the stimulus at the stimulus start time and output the stimulus at the intensity indicated by the pattern generated.

12 Claims, 15 Drawing Sheets

(56) References Cited

U.S. PATENT DOCUMENTS

| | | | |
|---|---|---|---|
| 2003/0080872 A1* | 5/2003 | Gutta | G04G 13/021 340/691.3 |
| 2003/0095476 A1* | 5/2003 | Mollicone | A61M 21/00 368/73 |
| 2003/0142591 A1* | 7/2003 | Baweja | G04G 13/02 368/263 |
| 2005/0104720 A1* | 5/2005 | Chon | G04G 13/023 340/691.3 |
| 2011/0160619 A1* | 6/2011 | Gabara | A61B 5/4806 600/595 |
| 2012/0137406 A1* | 6/2012 | Hide | A61M 21/00 2/206 |
| 2012/0163136 A1* | 6/2012 | Du | G04G 21/02 368/250 |
| 2012/0289867 A1* | 11/2012 | Kasama | A61B 5/0059 600/595 |
| 2013/0114382 A1 | 5/2013 | Xu | |
| 2013/0154838 A1* | 6/2013 | Alameh | G04G 13/023 340/575 |
| 2015/0067613 A1* | 3/2015 | Kim | G04G 13/026 715/863 |
| 2015/0348390 A1* | 12/2015 | Berezhnyy | G04G 13/023 340/309.7 |
| 2015/0378319 A1* | 12/2015 | Yamakawa | G04C 3/14 368/227 |
| 2016/0354040 A1* | 12/2016 | Aarts | A61M 16/0683 |
| 2019/0318283 A1* | 10/2019 | Kelly | G06Q 10/1095 |
| 2020/0090486 A1* | 3/2020 | Laakkonen | G08B 21/06 |
| 2022/0401689 A1* | 12/2022 | Campanella | A61M 21/00 |

FOREIGN PATENT DOCUMENTS

| | | |
|---|---|---|
| JP | 2010-244275 A | 10/2010 |
| JP | 2011-081114 A | 4/2011 |
| JP | 2014-509734 A | 4/2014 |
| JP | 2017-055302 A | 3/2017 |
| JP | 2018-082417 A | 5/2018 |

* cited by examiner

| Start time minute numerical value | Extension/ contraction rate range | Range of time required to reach maximum volume | Evaluation value |
|---|---|---|---|
| 0 | 1 ~ 6 | 10 ~ 60 sec. | 4 |
| 30 | 1 ~ 4 | 10 ~ 40 sec. | 3 |
| 15, 45 | 1 ~ 2 | 10 ~ 20 sec. | 2 |
| 10, 20, 40, 50 | 1 ~ 1.5 | 10 ~ 15 sec. | 1 |
| Other | 1 | 10 sec. | 0 |

CONTROL METHOD, CONTROL DEVICE, AND RECORDING MEDIUM

CROSS-REFERENCE OF RELATED APPLICATIONS

This application is the U.S. National Phase under 35 U.S.C. § 371 of International Patent Application No. PCT/JP2020/046128, filed on Dec. 10, 2020, which in turn claims the benefit of Japanese Application No. 2020-031221, filed on Feb. 27, 2020, the entire disclosures of which Applications are incorporated by reference herein.

TECHNICAL FIELD

The present disclosure relates to a control method, a control device, and a recording medium.

BACKGROUND ART

There is a conventional system which senses a state of a user while the user is sleeping and presents information pertaining to sleep or advice information after the user wakes up. Information or advice information to be presented to a plurality of users is generated by a server.

There is a conventional technique in which processing for each of a plurality of users is executed by a server (see Patent Literature (PTL) 1).

CITATION LIST

Patent Literature

[PTL 1] Japanese Unexamined Patent Application Publication No. 2018-82417

SUMMARY OF INVENTION

Technical Problem

However, there is a problem in that if the timings at which the server executes the processing for each of the plurality of users are close together, the load on the server will increase at that timing.

Accordingly, the present disclosure provides a control method and the like that suppress an increase in a load on a server.

Solution to Problem

A control method according to the present disclosure is a control method executed by a computer to control a device that outputs a stimulus to a user. The control method includes: obtaining a stimulus start time that is a time when the device is to start outputting the stimulus; determining whether or not the stimulus start time obtained satisfies a predetermined condition; generating a pattern extended or contracted in a time direction from an initial pattern indicating a timewise change in an intensity of the stimulus when the stimulus start time obtained is determined to satisfy the predetermined condition; and controlling the device to start outputting the stimulus at the stimulus start time and output the stimulus at the intensity indicated by the pattern generated.

According to this aspect, when the stimulus start time obtained from the user satisfies the predetermined condition, the stimulus is output in a pattern extended or contracted from the initial pattern, and thus the timing of the user's activity based on the output stimulus (specifically, waking up) can be distributed over time. Then, when the server executes processing based on the user's activity, the timing of the processing executed by the server can be distributed, which makes it possible to suppress an increase in the load on the server. In this manner, the control method according to the present disclosure makes it possible to suppress an increase in the load on the server.

If, for example, the timing at which the start the output of the stimulus is distributed in order to distribute the timing at which the server executes the processing, there may be cases where the output of the stimulus is started after the stimulus start time has passed. In such a case, the output of the stimulus not starting even after the desired stimulus start time is reached may cause the user to assume that there is a problem with the system. It is therefore not appropriate to distribute the timing at which the output of the stimulus starts in order to distribute the timing of the processing executed by the server. The control method according to the present disclosure has an effect in that an increase in the load on the server can be suppressed without performing such inappropriate processing.

Additionally, the determining may include using, as the predetermined condition, a condition that the stimulus start time obtained is a time determined in advance as a time having a relatively high probability of being set as the stimulus start time by users of each of a plurality of devices each being the device.

According to this aspect, the timing of the processing executed by the server can be distributed when a time having a relatively high probability of being set as the stimulus start time by a plurality of users is set. A time having a relatively high probability of being set as the stimulus start time by a plurality of users can be set as the stimulus start time by many users. This makes it easy for the load on the server to increase at that time. Accordingly, when the stimulus start time obtained from the user is a time having a relatively high probability of being set as the stimulus start time by a plurality of users, outputting the stimulus in a pattern extended from the initial pattern makes it possible to distribute the timing of the processing executed by the server. In this manner, the control method according to the present disclosure makes it possible to suppress an increase in the load on the server.

Additionally, the determining may include using, as the predetermined condition, a condition that a numerical value of a unit of minutes when the stimulus start time obtained is expressed in hour/minute/second format is 0, an integral multiple of 10, or an integral multiple of 15.

According to this aspect, a time in which, specifically, the numerical value of the unit of minutes, when the time is expressed in hour/minute/second format, is an integral multiple of 0 or 10, or an integral multiple of 15, is used as the time having a relatively high probability of being set as the stimulus start time by a plurality of users, and thus whether or not the time has a relatively high probability of being set as the stimulus start time by a plurality of users can be determined more easily. In this manner, the control method according to the present disclosure makes it possible to suppress an increase in the load on the server more easily.

Additionally, the determining may further include setting a range of an extension/contraction rate in accordance with the stimulus start time obtained. The setting of the range of the extension/contraction rate may include: setting a first range as the range of the extension/contraction rate when the numerical value of the unit of minutes is 0, when the stimulus start time is expressed in the hour/minute/second format; setting a second range smaller than the first range as the range of the extension/contraction rate when the numerical value of the unit of minutes is 30, when the stimulus start time is expressed in the hour/minute/second format; setting a third range smaller than the second range as the range of the extension/contraction rate when the numerical value of the unit of minutes is 15 or 45, when the stimulus start time is expressed in the hour/minute/second format; and setting a fourth range smaller than the third range as the range of the extension/contraction rate when the numerical value of the unit of minutes is 10, 20, 40, or 50, when the stimulus start time is expressed in the hour/minute/second format. The generating of the pattern may include generating the pattern using an extension/contraction rate that is within the range of the extension/contraction rate set.

According to this aspect, when the time has a relatively high probability of being set as the stimulus start time by a plurality of users, the pattern is generated in accordance with the numerical value of the unit of minutes. A pattern extended using a higher extension/contraction rate is generated as the probability increases. Accordingly, the extension/contraction rate of the pattern increases as times for the stimulus start time are set which are likely to increase the load on the server, and the effect of distributing the load on the server can be increased. In this manner, the control method according to the present disclosure makes it possible to suppress an increase in the load on the server adaptively in accordance with the stimulus start time which has been set.

Additionally, the generating of the pattern may include randomly selecting one extension/contraction rate among a plurality of extension/contraction rates that are within the range of the extension/contraction rate set, and generating the pattern using the one extension/contraction rate selected.

According to this aspect, the pattern is generated using an extension/contraction rate which has been selected at random from the set extension/contraction rate range, which makes it possible to increase the effect of distributing the load on the server. As such, the control method according to the present disclosure makes it possible to further suppress an increase in the load on the server.

Additionally, the initial pattern may be a pattern in which the intensity of the stimulus stays constant or increases as time passes.

According to this aspect, a pattern in which the intensity of the stimulus stays constant or increases as time passes is used as the initial pattern, and the stimulus is output to the user using a pattern generated from the initial pattern. Accordingly, the control method according to the present disclosure makes it possible to suppress an increase in the load on the server more easily.

Additionally, the initial pattern may be a pattern in which: (a) the intensity of the stimulus increases from 0 at the stimulus start time; (b) the intensity of the stimulus increases and decreases in a range greater than 0 and less than a predetermined intensity until a predetermined length of time passes after the stimulus start time; and (c) the intensity of the stimulus stays at the predetermined intensity after the predetermined length of time passes after the stimulus start time.

According to this aspect, a pattern that ultimately stimulates the user at a maximum intensity after increasing or decreasing partway through is used as the initial pattern, and the stimulus is output to the user using a pattern generated from the initial pattern. Accordingly, the control method according to the present disclosure makes it possible to suppress an increase in the load on the server more easily.

Additionally, when an operation to stop the stimulus is accepted from the user, the device may obtain, through communication with a server, information to be presented to the user, and the information obtained may be presented to the user.

According to this aspect, an increase in the load caused by communication processing and processing for generating the presentation information, executed by the server after accepting an operation from the user, is suppressed. As such, the control method according to the present disclosure makes it possible to suppress an increase in the load from processing including the communication processing and generation processing performed by the server.

Additionally, the stimulus may be a stimulus prompting the user to wake up.

According to this aspect, processing performed by the server for outputting a stimulus prompting the user to wake up and presenting presentation information to the user who has woken up based on the output stimulus can be distributed over time. As such, the control method according to the present disclosure makes it possible to suppress an increase in the load on the server.

Additionally, the stimulus may include any one of sound, light, temperature, wind, or vibration.

According to this aspect, any one of sound, light, temperature, wind, or vibration is used as the stimulus. Accordingly, the control method according to the present disclosure can suppress an increase in the load on the server while using any one of sound, light, temperature, wind, or vibration as the stimulus.

Additionally, a control device according to the present disclosure is a control device that controls a device that outputs a stimulus to a user. The control device includes: an obtainer that obtains a stimulus start time that is a time when the device is to start outputting the stimulus; a generator that determines whether or not the stimulus start time obtained satisfies a predetermined condition, and generates a pattern extended or contracted in a time direction from an initial pattern indicating a timewise change in an intensity of the stimulus when the stimulus start time obtained is determined to satisfy the predetermined condition; and a controller that controls the device to start outputting the stimulus at the stimulus start time and output the stimulus at the intensity indicated by the pattern generated.

This aspect provides the same effects as the above-described control method.

Note that these comprehensive or specific aspects may be realized by a system, a device, an integrated circuit, a computer program, or a computer-readable recording medium such as a CD-ROM, or may be implemented by any desired combination of systems, devices, integrated circuits, computer programs, and recording media.

Advantageous Effects of Invention

The control method according to the present disclosure makes it possible to suppress an increase in a load on a server.

DESCRIPTION OF EMBODIMENTS

Embodiments will be described in detail hereinafter with reference to the drawings where appropriate. There are, however, cases where descriptions are omitted when further detail is not necessary. For example, detailed descriptions of matters which are already well-known, redundant descriptions of substantially identical configurations, and so on may be omitted. This is to avoid unnecessary redundancy in the descriptions and facilitate understanding for those skilled in the art.

Note that the inventor(s) have provided the accompanying drawings and the following descriptions primarily so that those skilled in the art can sufficiently understand the present disclosure, and as such the content of the scope of claims is not intended to be limited by the drawings and descriptions in any way.

In the following, the background to the present invention and the problems to be solved by the invention will be described in detail, followed by descriptions of an embodiment.

EMBODIMENT

The present embodiment will describe a control method and the like which suppress an increase in a load on a server.

Figure 1:
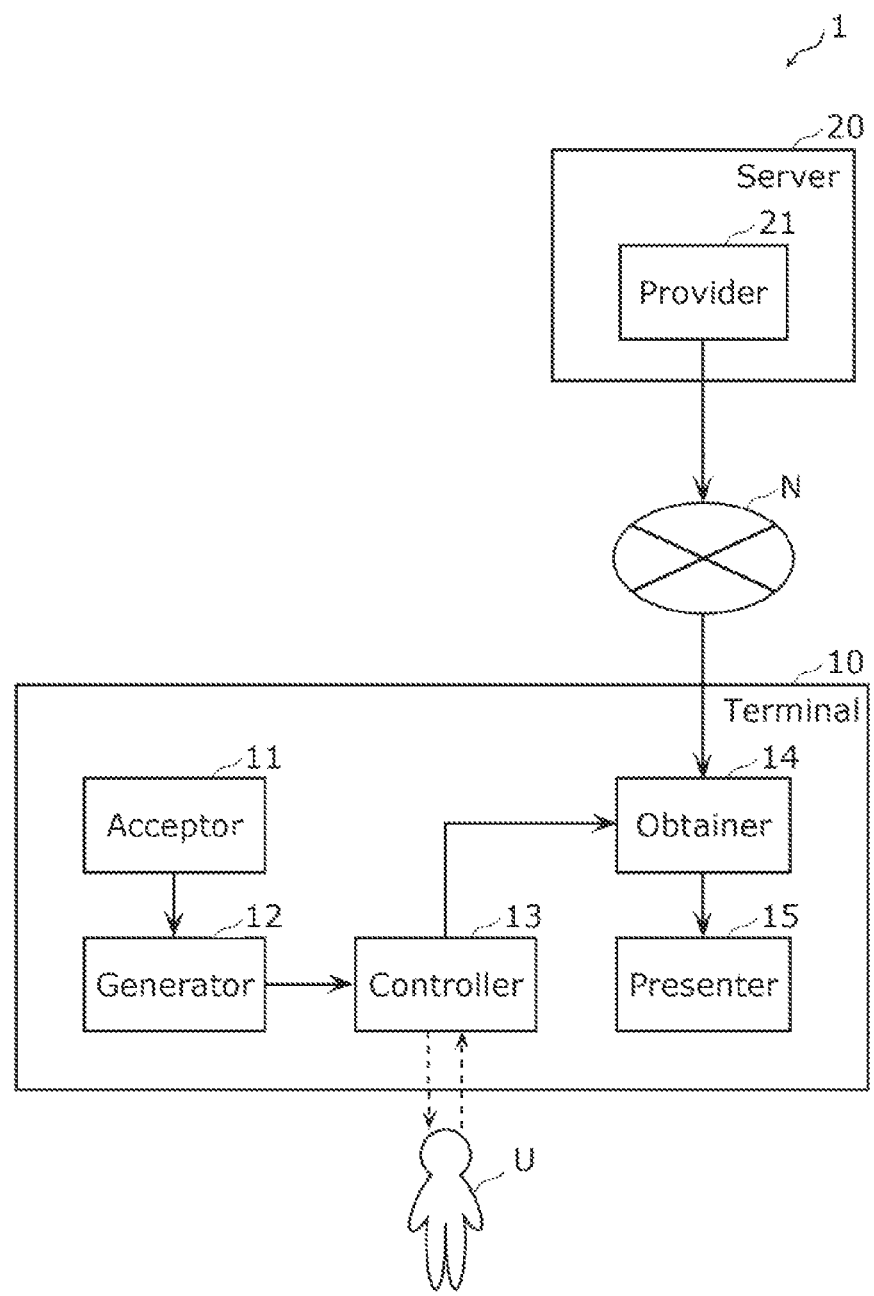
FIG. 1 is a descriptive diagram schematically illustrating the configuration of a system according to an embodiment.

FIG. 1 is a descriptive diagram schematically illustrating the configuration of system 1 according to the present embodiment. System 1 illustrated in FIG. 1 is a system that prompts user U to take action by stimulating user U and then presents information to user U. More specifically, system 1 is an example of a system that wakes up a sleeping user U by outputting an alarm sound and changing the volume thereof, and presents information or advice information pertaining to sleep after user U wakes up.

Here, the information presented to user U is also referred to as "presentation information" for user U. The presentation information is generated by a server based on information indicating body movement of user U when sleeping and the like, and is presented to user U by a terminal owned by user U.

Here, the alarm sound is an example of a stimulus to user U. Although this case is described as an example, the stimulus to user U may include any one of sound, light, temperature, wind (more generally, air movement) or vibration, and may also include changes in the presence or intensity of any one of sound, light, temperature, wind, or vibration. The stimulus to user U includes, but is not limited to, a stimulus to wake up user U.

As illustrated in FIG. 1, system 1 includes terminal 10 and server 20. Terminal 10 and server 20 are communicably connected over network N.

Terminal 10 is a communication terminal owned by user U. Terminal 10 accepts, from user U, a start time at which the alarm sound for waking up is to be output, and outputs the alarm sound when the start time arrives. When an operation for stopping the output of the alarm sound is accepted from user U, the output of the alarm sound is stopped, and the presentation information for user U is presented using an image, sound, or the like. Terminal 10 is an example of a device that outputs a stimulus to user U. Terminal 10 is placed in a location where the output alarm sound can reach user U, e.g., on the bedding of user U when sleeping. Terminal 10 is a mobile terminal implemented by a computer, such as a smartphone or a tablet, for example.

Server 20 generates the presentation information. Server 20 includes provider 21 that generates the presentation information to be presented to user U and provides the presentation information to terminal 10. When information indicating body movement of user U when sleeping is obtained, server 20 presents the presentation information by having provider 21 transmit the presentation information to terminal 10.

Terminal 10 will be described in further detail.

As illustrated in FIG. 1, terminal 10 includes acceptor 11, generator 12, controller 13, obtainer 14, and presenter 15. The function units of terminal 10 can be realized by a Central Processing Unit (CPU) executing programs using memory.

Acceptor 11 is a processing unit that accepts the start time, which is the time when terminal 10 is to start outputting the alarm sound. Acceptor 11 accepts a user operation for setting the start time through a suitable user interface device (UI device). For example, acceptor 11 accepts a touch operation made by the user on a screen or the like of terminal 10 through a touch panel-type display serving as the UI device. Acceptor 11 also accepts voice operations made by the user through a microphone serving as the UI device. The start time is an example of a stimulus start time, which is a time at which the output of a stimulus is to be started.

Generator 12 is a processing unit that generates a pattern indicating a timewise change in the volume of the alarm sound (also called simply a "pattern"). Specifically, generator 12 determines whether or not the start time obtained by acceptor 11 satisfies a predetermined condition, and if the start time obtained satisfies the predetermined condition, generates a pattern that is extended/contracted in the time direction from an initial pattern indicating the timewise change in the volume of the alarm sound. A variety of conditions can be used for the predetermined condition, and examples will be given below.

For example, generator 12 may use, as the predetermined condition, the condition that the start time obtained by acceptor 11 is a predetermined time in the aforementioned determination, as a time that has a relatively high probability of being set as the start time by the users of each of a plurality of terminals 10. More specifically, generator 12 may use the condition that the numerical value of the unit of minutes when the start time obtained by acceptor 11 is expressed in hour/minute/second format is 0, an integral multiple of 10, or an integral multiple of 15 as the predetermined condition in the aforementioned determination. In addition, the condition that the numerical value of the minute unit when the start time is expressed in hour/minute/second format is an integral multiple of 5 may be added to the aforementioned condition. The pattern generated by generator 12 will be described in detail later.

Controller 13 is a processing unit that controls the output of the alarm sound by terminal 10. Controller 13 performs control for starting the output of the alarm sound at the start time, and outputting the alarm sound at the intensity (i.e., volume) indicated by the pattern generated by generator 12.

Additionally, when an operation for stopping the output of the alarm sound is received from user U, controller 13 performs control for stopping the output of the alarm sound.

Obtainer 14 is a processing unit that obtains the presentation information from server 20. When an operation for stopping the output of the alarm sound is accepted from user U, obtainer 14 transmits a request for the presentation information to be presented to user U to server 20, and obtains the presentation information transmitted by server 20 in response to the request.

Presenter 15 is a processing unit that presents the presentation information to user U. Presenter 15 presents the presentation information obtained by obtainer 14 to the user using the UI device. Specifically, presenter 15 presents the presentation information to user U by displaying the information in a screen serving as the UI device or outputting the information as audio using a speaker serving as the UI device.

Figure 2:
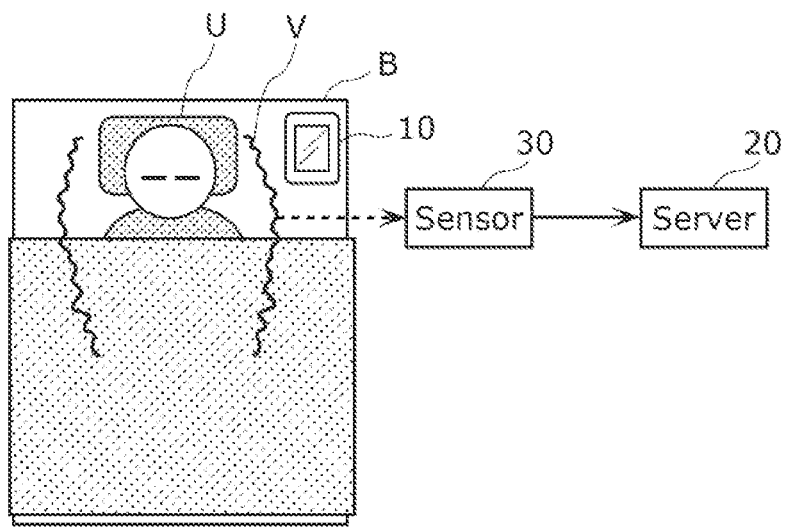
FIG. 2 is a descriptive diagram illustrating a usage example of the system, and an example of the obtainment of a sensor value obtained by a server, according to the embodiment.

FIG. 2 is a descriptive diagram illustrating a usage example of system 1, and an example of the obtainment of a sensor value obtained by server 20, according to the present embodiment. An example in which vibrations produced by body movements of user U while sleeping will be described here.

FIG. 2 illustrates user U who is sleeping in bedding B. Terminal 10 is, for example, placed on the bedding of the sleeping user U. Vibrations V arise in bedding B as the body of sleeping user U moves. Sensor 30 detects vibrations V in bedding B, generates a sensor value, and transmits the generated sensor value to server 20. When a pre-set time arrives, terminal 10 outputs the alarm sound and prompts the user to wake up.

When user U wakes up, server 20 receives the sensor value detected by sensor 30, estimates timewise changes in the depth of user U's sleep, for example, and generates the presentation information for user U. Note that sensor 30 may be a vibration sensor embedded in bedding B, or may be a vibration sensor included in terminal 10 which is placed on bedding B. Additionally, sensor 30 may be a pressure sensor that measures pressure on the bedding. Sensor 30 may be a sensor that emits radio waves toward the user, measures the intensity, frequency, or the like of reflected radio waves, and measures changes in the expansion and contraction of the user's body.

Additionally, sensor 30 may transmit the raw values of measured values to server 20. Additionally, instead of the raw data of measured data, sensor 30 may transmit data processed on the basis of the stated data to server 20. The frequency of the user's breathing, the heart rate or heartbeat variability, or the like calculated from the values of the measured vibrations, radio wave intensity or frequency values, variability, and the like can be given as examples of the processed data.

For example, if the vibrations are measured using an accelerometer or a gyrosensor, an amount of body movement of the user is calculated based on the measured vibrations, and the depth of the user's sleep can be calculated based on the amount of body movement. Additionally, if the expansion and contraction of the user's body, blood vessels, or pulse is measured using a radio wave sensor or a piezoelectric sensor, the amount of the user's breathing rate or heart rate, changes therein, and the like can be calculated based on the measured expansion and contraction, which makes it possible to calculate the depth of the user's sleep.

Figure 3:
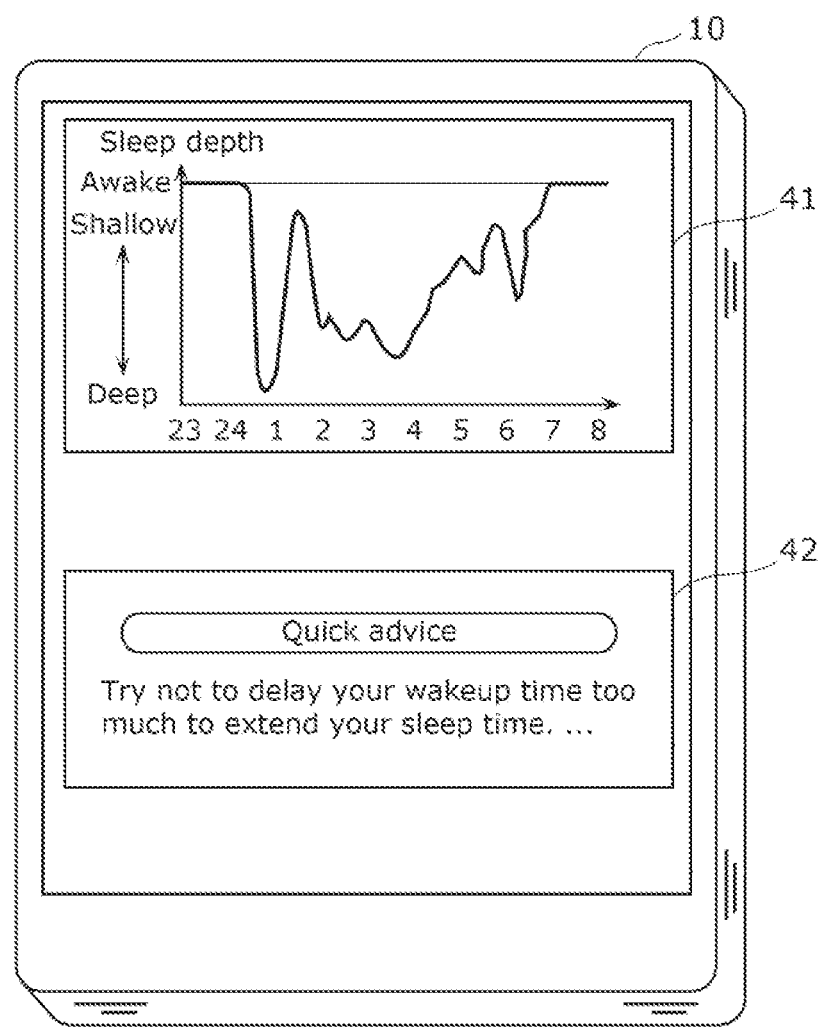
FIG. 3 is a descriptive diagram illustrating an example of presentation information according to the embodiment.

FIG. 3 is a descriptive diagram illustrating an example of the presentation information according to the present embodiment.

FIG. 3 illustrates an example of the presentation information displayed in the screen of terminal 10.

The presentation information illustrated in FIG. 3 includes image 41 of a graph in an upper part of the screen, with the horizontal axis representing time and the vertical axis representing the depth of user U's sleep, and includes image 42 indicating advice information pertaining to user U's sleep in a lower part of the screen.

By viewing the presentation information displayed in terminal 10, user U can know their own sleep depth as well as the advice information pertaining to their sleep, which can lead to better sleep.

Figures 4, 5:
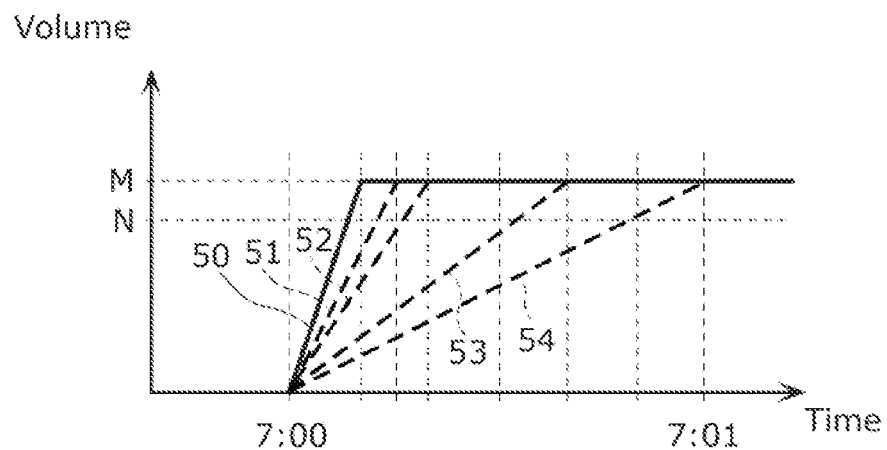
FIG. 4 is a descriptive diagram of an extension/contraction rate range according to the embodiment.
FIG. 5 is a descriptive diagram illustrating a timewise change in a volume controlled by a controller according to the embodiment.

FIG. 4 is a descriptive diagram of an extension/contraction rate range according to the present embodiment. The extension/contraction rate range illustrated in FIG. 4 is used by generator 12 to generate a pattern.

As illustrated in FIG. 4, the extension/contraction rate range is determined in accordance with the numerical value of the unit of minutes of the start time accepted by acceptor 11 from user U (also called simply the "minute numerical value"). Additionally, in FIG. 4, the range of time required until a maximum volume is reached is associated with an evaluation value in accordance with the minute numerical value of the start time accepted by acceptor 11 from user U.

Specifically, "0" for the minute numerical value of the start time is associated with "1-6" (corresponding to a first range) as the extension/contraction rate range. If the time required to reach the maximum volume from the start is 10 seconds in the initial pattern, the range of the time required to reach the maximum volume from the start in the pattern generated by generator 12 is 10 seconds to 60 seconds.

Likewise, "30", "15 or 45", and "10, 20, 40, or 50" as the minute numerical values of the start time are associated with "1-4" (corresponding to a second range), "1-2" (corresponding to a third range), and "1-1.5" (corresponding to a fourth range) as the extension/contraction rate range, respectively. If the time required to reach the maximum volume from the start is 10 seconds in the initial pattern, the ranges of the time required to reach the maximum volume from the start in the pattern generated by generator 12 are "10-40 seconds", "10-20 seconds", and "10-15 seconds", respectively.

If the minute numerical value of the start time is "other", i.e., a start time other than the above, the extension/contraction rate range is 1, and the time required to reach the maximum volume from the start is 10 seconds, as in the initial pattern.

Additionally, the evaluation value is defined as how good the timing of the minute numerical value is when the start time is expressed in the hour/minute/second format. A greater numerical value for the evaluation value indicates a better timing. Here, "good timing" also means a good cutoff point, and is generally a time that is easy for user U to remember, easy to use as a reference for taking action, and easy to use as a way to segment time.

Here, as one example, the minute numerical value of the start time is classified into five groups, i.e., "0", "30", "15 or 45", "10, 20, 40, or 50", and "other". In this case, "0" represents the best timing, and the evaluation value is set to 4. Meanwhile, "other" represents the worst timing, and the evaluation value is set to 0. Evaluation values are set to 3, 2, and 1 for "30", "15 or 45", and "10, 20, 40, or 50", indicating progressively worse timings.

In general, there is a high probability that user U will set a good timing for the time to start outputting the alarm sound for waking up, and the better the timing is, the higher the probability is that the stated time will be set. Thus the "evaluation value for how good the timing is" can be said to indicate the probability of the user setting that time as the start time.

FIG. 5 is a descriptive diagram illustrating a timewise change in the volume controlled by controller 13 according to the present embodiment.

As illustrated in FIG. 5, the horizontal axis represents time and the vertical axis represents the volume of the alarm sound, and patterns 50, 51, 52, 53, and 54 are shown for the timewise change in the volume.

Volume M on the vertical axis indicates the maximum volume, whereas volume N represents 70 to 80% of the maximum volume, which is the volume at which user U is expected to wake up.

Pattern 50 is an example of the initial pattern. Pattern 50 is a pattern in which the volume increases at a constant rate from 7:00, which is the start time, reaches the maximum volume at 7:00:10, and then stays at the maximum volume thereafter. In other words, pattern 50 is a pattern in which the volume increases linearly as time passes from the start time, reaches the maximum volume, and then stays at the maximum volume thereafter. The initial pattern is a pattern set in advance, and is a standard pattern used when generating the patterns described below. Pattern 50 is also a pattern generated by generator 12 when the minute numerical value of the start time is "other".

Note that the initial pattern may be a pattern in which the volume of the alarm sound (and more generally, the intensity of the stimulus) stays constant or increases over time. In the initial pattern, the volume of the alarm sound at times after the start time may have a characteristic of being louder than the volume of the alarm sound at the start time.

Additionally, the initial pattern may be a pattern in which (a) at the start time, the intensity of the stimulus increases from 0, (b) from the stimulus start time, the intensity of the stimulus increases or decreases in a range greater than 0 and less than a predetermined intensity until a predetermined amount of time elapses, and (c) after the predetermined amount of time has elapsed following the stimulus start time, the intensity of the stimulus stays at the predetermined intensity. The predetermined amount of time can be a granularity of time that can be set as the start time, e.g., one minute.

Patterns 51 to 54 are examples of patterns that have been extended in the time direction from the initial pattern, and are generated by generator 12 corresponding to the minute numerical value of the start time. Each of patterns 51 to 54 will be described hereinafter.

Pattern 51 is a pattern in which pattern 50 has been extended 1.5 times in the time direction. Pattern 51 has the longest extension in the time direction among the patterns generated by generator 12 when the minute numerical value of the start time is "10, 20, 40 or 50". In other words, when the minute numerical value of the start time is "10, 20, 40 or 50", generator 12 generates a pattern that is extended (i.e., elongated) from the initial pattern at an extension/contraction rate between pattern 50 and pattern 51.

Pattern 52 is a pattern in which pattern 50 has been extended 2× in the time direction. Pattern 52 has the longest extension in the time direction among the patterns generated by generator 12 when the minute numerical value of the start time is "15 or 45". In other words, when the minute numerical value of the start time is "15 or 45", generator 12 generates a pattern that is extended (i.e., elongated) from the initial pattern at an extension/contraction rate between pattern 50 and pattern 52.

Pattern 53 is a pattern in which pattern 50 has been extended 4× in the time direction. Pattern 53 has the longest extension in the time direction among the patterns generated by generator 12 when the minute numerical value of the start time is "30". In other words, when the minute numerical value of the start time is "30", generator 12 generates a pattern that is extended (i.e., elongated) from the initial pattern at an extension/contraction rate between pattern 50 and pattern 53.

Pattern 54 is a pattern in which pattern 50 has been extended 6× in the time direction. Pattern 54 has the longest extension in the time direction among the patterns generated by generator 12 when the minute numerical value of the start time is "0". In other words, when the minute numerical value of the start time is "0", generator 12 generates a pattern that is extended (i.e., elongated) from the initial pattern at an extension/contraction rate between pattern 50 and pattern 54.

To rephrase, generator 12 generates patterns 51 to 54 by reducing the slope or gradient of the change in the volume of the alarm sound, using pattern 50 as a reference.

In this manner, generator 12 may set the first range as the extension/contraction rate range when the numerical value of the minute unit when the start time is expressed in the hour/minute/second format is 0, set the second range when the numerical value of the minute unit is 30, set the third range when the numerical value of the minute unit is 15 or 45, and set the fourth range when the numerical value of the minute unit is 10, 20, 40, or 50. Here, the first range, the second range, the third range, and the fourth range are set to become smaller in that order.

In this way, if user U sets a time that has a relatively high probability of being set as the start time, the initial pattern can be extended within a broader range, which increases the effect of distributing the timing of subsequent processing by server 20. If user U sets a time that has a relatively low probability of being set as the start time, the initial pattern can be extended within a narrower range, which prompts user U to wake up earlier.

Note that when generating the patterns as described above, generator 12 may set the pattern by randomly setting the extension/contraction rate between pattern 50 and any of patterns 51 to 54. To realize this random setting, an ideal random value may be used, or a pseudo-random value may be used. In addition, a numerical value in the unit of milliseconds may be used as the random value when the timing at which the start time is set by the user is expressed in the hour/minute/second format.

Processing by system 1 having the foregoing configuration will be described next.

Figure 6:
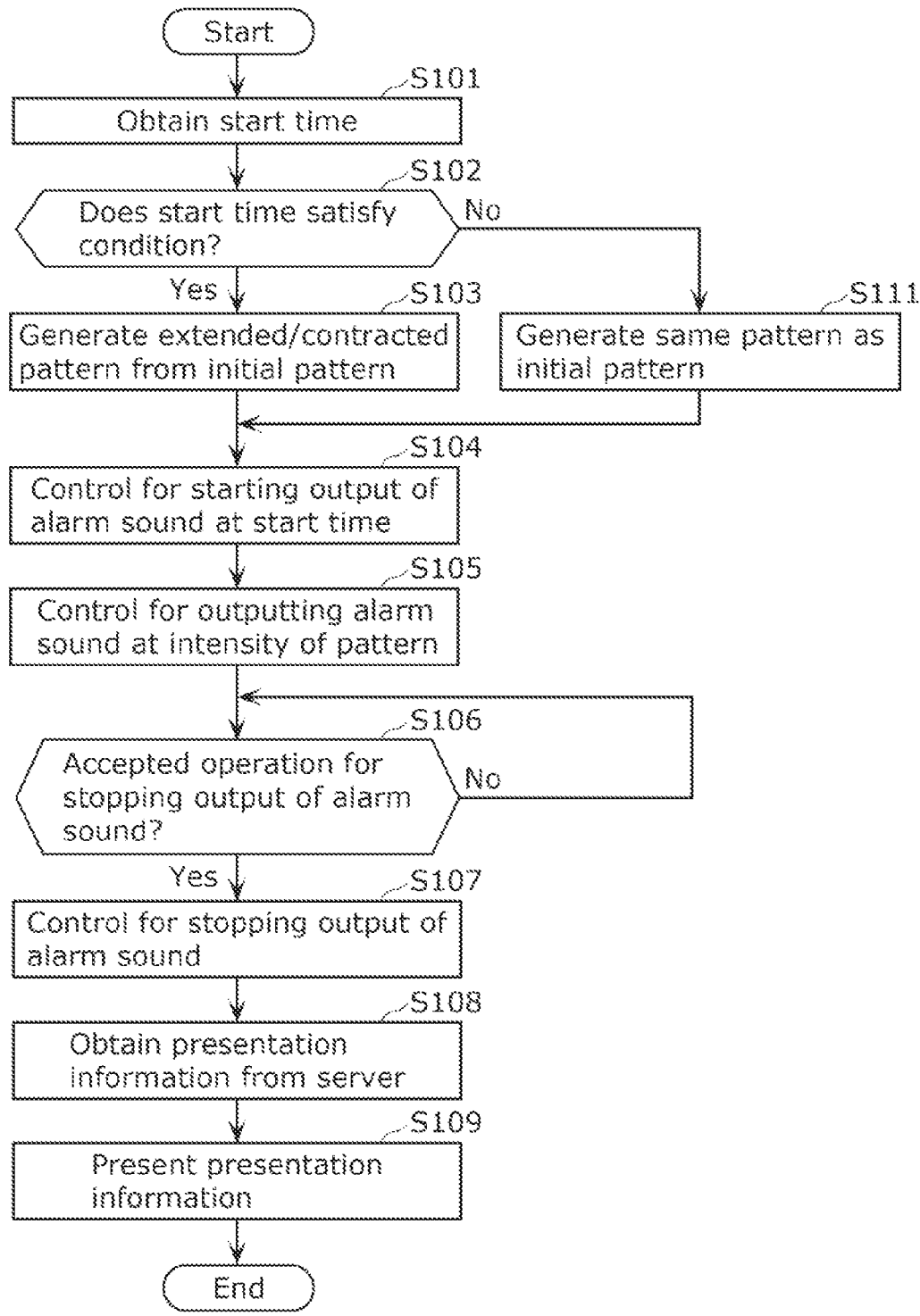
FIG. 6 is a flowchart illustrating processing executed by the system according to the embodiment.

FIG. 6 is a flowchart illustrating the processing executed by system 1 according to the present embodiment. The flowchart in FIG. 6 illustrates a control method for controlling a device that outputs a stimulus to a user.

In step S101, acceptor 11 obtains the start time from user U.

In step S102, generator 12 determines whether or not the start time accepted by acceptor 11 in step S101 satisfies a predetermined condition. More specifically, generator 12 determines whether or not the start time accepted by acceptor 11 in step S101 is a time set in advance as a time having a good timing, e.g., whether the minute numerical value of the start time matches one of "0, 30, 15, 45, 10, 20, 40, or 50". If the start time satisfies the predetermined condition (Yes in step S102), the sequence moves to step S103, and if not (No in step S102), the sequence moves to step S111.

In step S103, generator 12 generates an extended pattern from the initial pattern. At this time, generator 12 may set a different extension/contraction rate according to the minute numerical value of the start time, and then generate an extended pattern using the set extension/contraction rate.

In step S111, generator 12 generates the same pattern as the initial pattern.

After the processing of step S103 or step S111 ends, the sequence moves to step S104.

In step S104, controller 13 performs control for starting the output of the alarm sound at the start time obtained in step S101.

In step S105, controller 13 controls the volume of the alarm sound at the intensity indicated by the pattern set in step S103. It is assumed that user U wakes up, i.e., transitions from a sleeping state to an awake state, and performs an operation for stopping the output of the alarm sound through terminal 10 in response to the alarm sound output in this manner.

In step S106, controller 13 determines whether or not the operation for stopping the output of the alarm sound has been accepted. If it is determined that an operation for stopping the output of the alarm sound has been accepted (Yes in step S106, the sequence moves to step S107, and if not (No in step S106), step S106 is executed again. In other words, controller 13 enters a standby state in step S106 until an operation for stopping the output of the alarm sound is accepted.

In step S107, controller 13 performs control for stopping the output of the alarm sound.

In step S108, obtainer 14 obtains the presentation information from server 20. At this time, server 20 executes communication processing involved with communication with terminal 10, and generation processing for generating the presentation information.

In step S109, presenter 15 presents the presentation information obtained in step S108.

Note that the processing of step S103 and step S111 may be performed at any timing between the obtainment of the start time (step S101) and the start of the output of the alarm sound (step S104). For example, the processing may be performed immediately after obtaining the start time, upon accepting an operation for activating the alarm from the user after obtaining the start time, or immediately before the start time.

The sequence of processing illustrated in FIG. 6 makes it possible for system 1 to suppress an increase in the load on server 20. Specifically, an increase in the load associated with the communication processing and generation processing performed by server 20 when step S108 is being executed can be suppressed.

The processing of the overall system 1 according to the present embodiment will be described next in comparison with a related technique.

Figure 7:
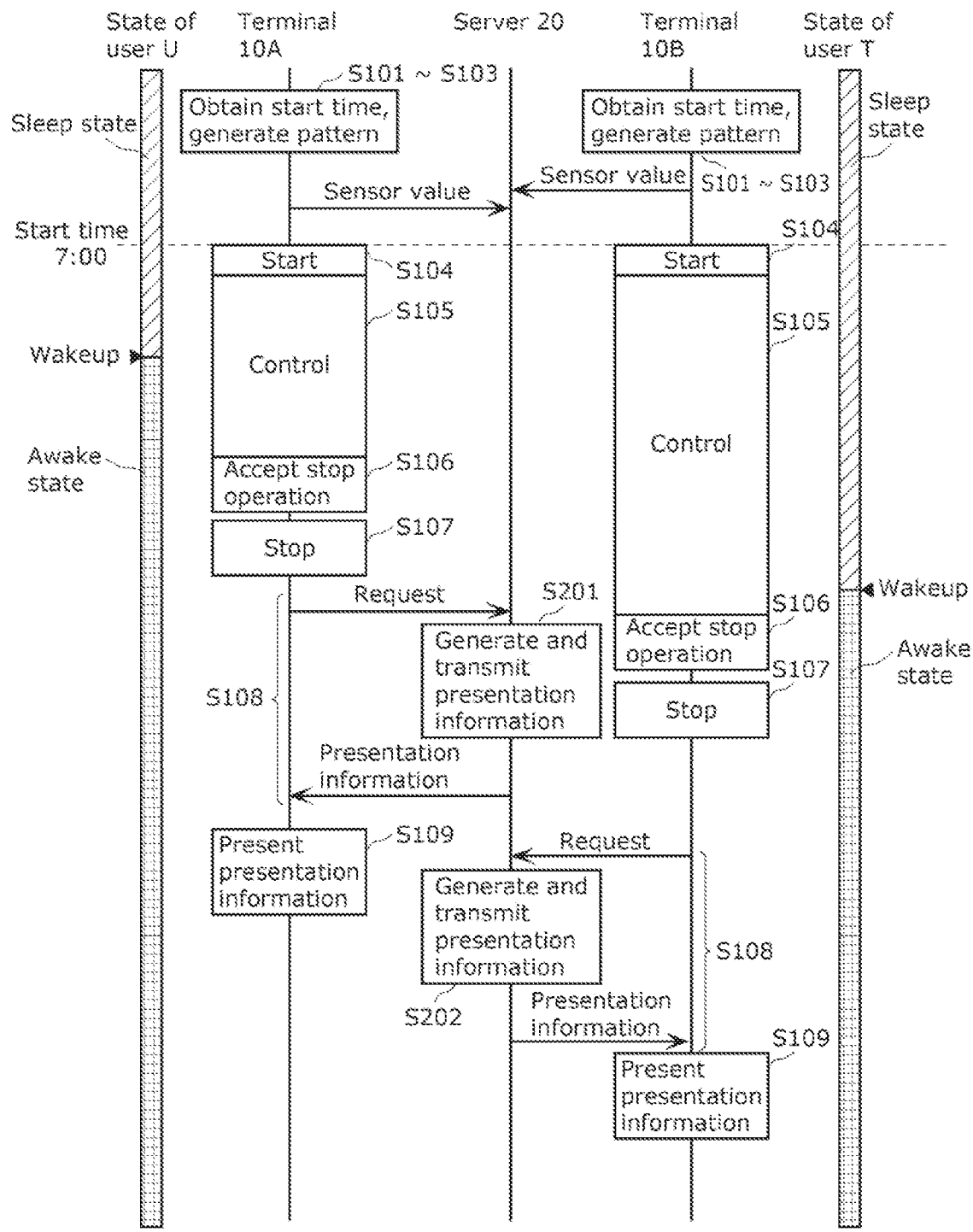
FIG. 7 is a sequence chart illustrating processing by the overall system according to the embodiment.

FIG. 7 is a sequence chart illustrating processing by the overall system 1 according to the present embodiment.

FIG. 7 illustrates an example in which server 20 generates the presentation information for two users U and T who have set the same start time, e.g., 7 AM. Note that the number of users is not limited to two, and may be several hundred, several tens of thousands, or more, and the effects of the present invention are more pronounced as the number of users increases.

FIG. 7 illustrates processing by terminal 10A, which is terminal 10 of user U; terminal 10B, which is terminal 10 of user T; and server 20. Additionally, whether users U and T are in the sleeping state or the awake state is indicated as well. Processing that is the same as the processing illustrated in FIG. 6 is given the same reference signs, and detailed descriptions thereof will be omitted.

When user U is sleeping, a sensor value indicating vibrations produced by user U's body movement is transmitted from terminal 10A to server 20. Likewise, when user T is sleeping, a sensor value indicating vibrations produced by user T's body movement is transmitted from terminal 10B to server 20. These may be transmitted every several minutes or every several tens of minutes, or may be transmitted at once immediately before step S104, for example.

Furthermore, the obtainment of the start times by terminals 10A and 10B, the generation of the pattern, and the like are complete by the time the start time arrives (steps S101 to S103). Here, because the start time is 7 AM, i.e., the minute numerical value is 0, a numerical value randomly selected from the range of 1 to 6 is used as the extension/contraction rate, and as a result, the patterns set by generator 12 of terminal 10A and generator 12 of terminal 10B are different. Here, assume that generator 12 of terminal 10A has set a pattern in which the volume of the alarm sound rises faster.

When the start time arrives, terminals 10A and 10B control the output of the alarm sound (steps S104 to S105). Controller 13 of terminal 10A increases the volume of the alarm sound relatively faster, and thus user U wakes up earlier than user T and performs an operation for stopping the output of the alarm sound after waking up. After receiving this stop operation and stopping the output of the alarm sound, terminal 10A makes a request to server 20 for the presentation information, and receives and displays the presentation information (steps S106 to S109).

When the request for the presentation information is sent from terminal 10A (step S108), server 20 generates the presentation information for user U based on the sensor value received from terminal 10A, and performs processing for transmitting the generated presentation information (step S201).

With respect to terminal 10B, controller 13 of terminal 10B increases the volume of the alarm sound relatively slower, and thus user T wakes up later than user U and performs an operation for stopping the output of the alarm sound after waking up. After receiving this stop operation and stopping the output of the alarm sound, terminal 10B makes a request to server 20 for the presentation information, and receives and displays the presentation information to user T (steps S106 to S109). Server 20 executes the same processing for terminal 10B as the above-described processing executed for terminal 10A (step S202).

The related technique for comparison with system 1 will be described next.

Figure 8:
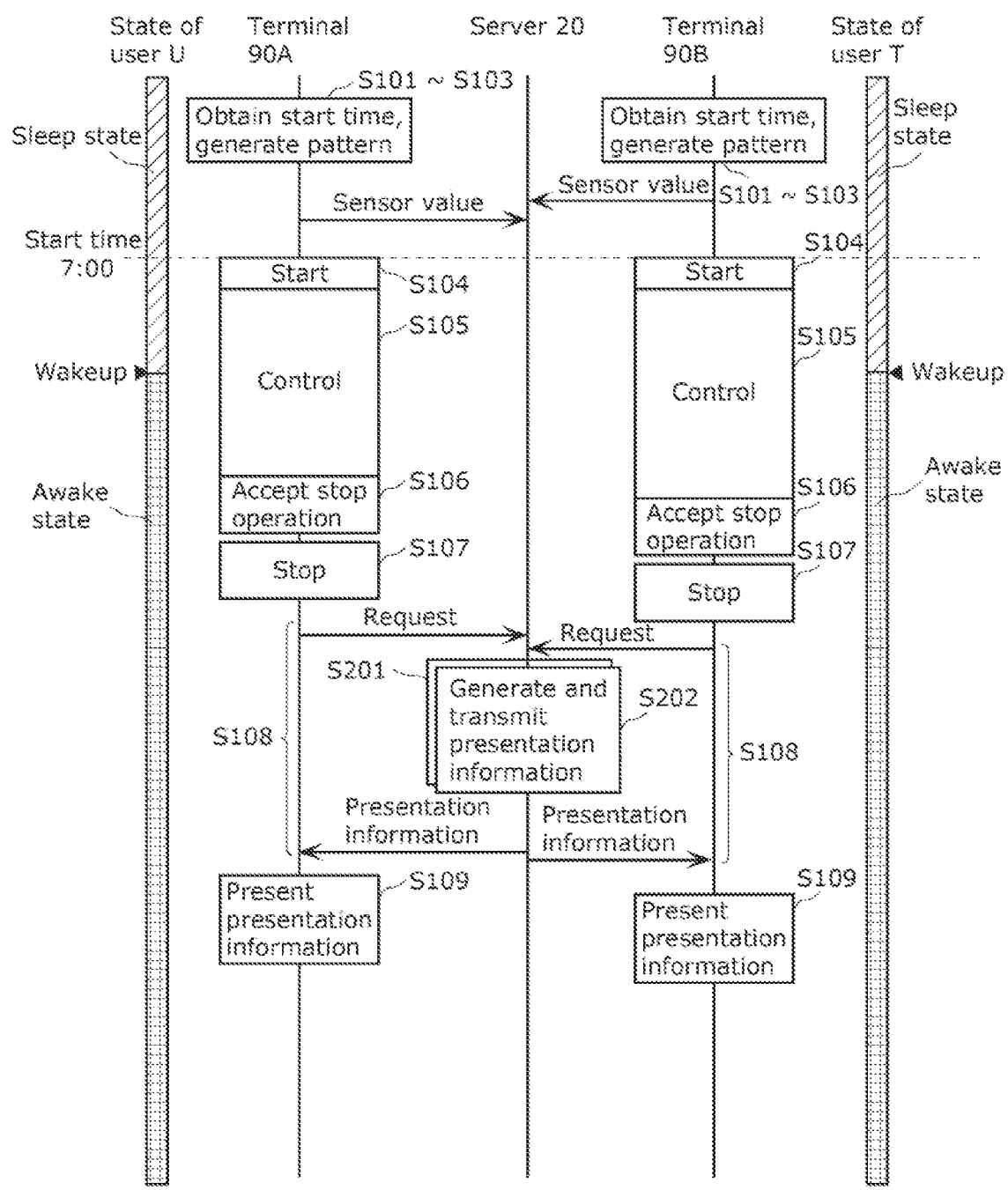
FIG. 8 is a sequence chart illustrating processing by an overall system according to a related technique.

FIG. 8 is a sequence chart illustrating processing by an overall system according to a related technique. Here, the "related technique" is a technique in which terminals 90A and 90B, which control the volume of the alarm sound at the same pattern regardless of whether or not the start time satisfies a predetermined condition, are used instead of terminals 10A and 10B of the present embodiment, and is an example of related art. Processing that is the same as that illustrated in FIG. 7 will be given the same reference signs, and detailed descriptions thereof will be omitted.

As in FIG. 7, FIG. 8 illustrates an example in which server 20 generates the presentation information for two users U and T who have set the same start time, i.e., 7 AM.

The obtainment of the start times by terminals 90A and 90B, the generation of the pattern, and the like are complete by the time the start time arrives (steps S101 to S103). At this time, the start time is 7 AM, i.e., the minute numerical value is 0, but generator 12 of terminal 90A and generator 12 of terminal 90B set patterns in which the speeds at which the volume of the alarm sound rises are the same.

When the start time arrives, terminals 90A and 90B start the output of the alarm sound, and control the output of the alarm sound according to the pattern (step S104). Because controller 13 of terminal 90A and controller 13 of terminal 90B control the volume of the alarm sound with the same pattern, users U and T wake up around the same timing, and then perform operations for stopping the output of the alarm sound of terminals 90A and 90B, respectively.

After receiving this stop operation and stopping the output of the alarm sound, terminals 90A and 90B make requests to server 20 for the presentation information, and receive and display the presentation information to users U and T, respectively (steps S106 to S109).

When the requests for the presentation information are sent from terminals 90A and 90B (step S108), server 20 generates the presentation information for user U and user T based on the sensor values received from terminals 90A and 90B, respectively, and performs processing for transmitting the generated presentation information (steps S201 and S202).

Here, because the patterns of terminals 90A and 90B are the same, the timing of the processing for generating the presentation information and the processing for transmitting the presentation information executed by the server, i.e., step S201 and step S202, are almost the same, and a problem will arise where the timings of the processing in the server will be close together. If the number of terminals rises to hundreds, tens of thousands, or more, the problem of the timings of the processing by the server being close will become even more pronounced.

On the other hand, according to the processing sequence illustrated in FIG. 7, because the patterns of terminals 10A and 10B are different, the timing of processing for generating the presentation information and the processing for transmitting the presentation information, performed by the server, are different from each other. In this manner, the timing of the processing by the server is distributed, and concentration of the load on the server load is suppressed.

Note that system 1 according to the present embodiment may be provided with a function that enables the pattern generated in step S103 or step S111 to be changed later through user operations.

Figure 9:
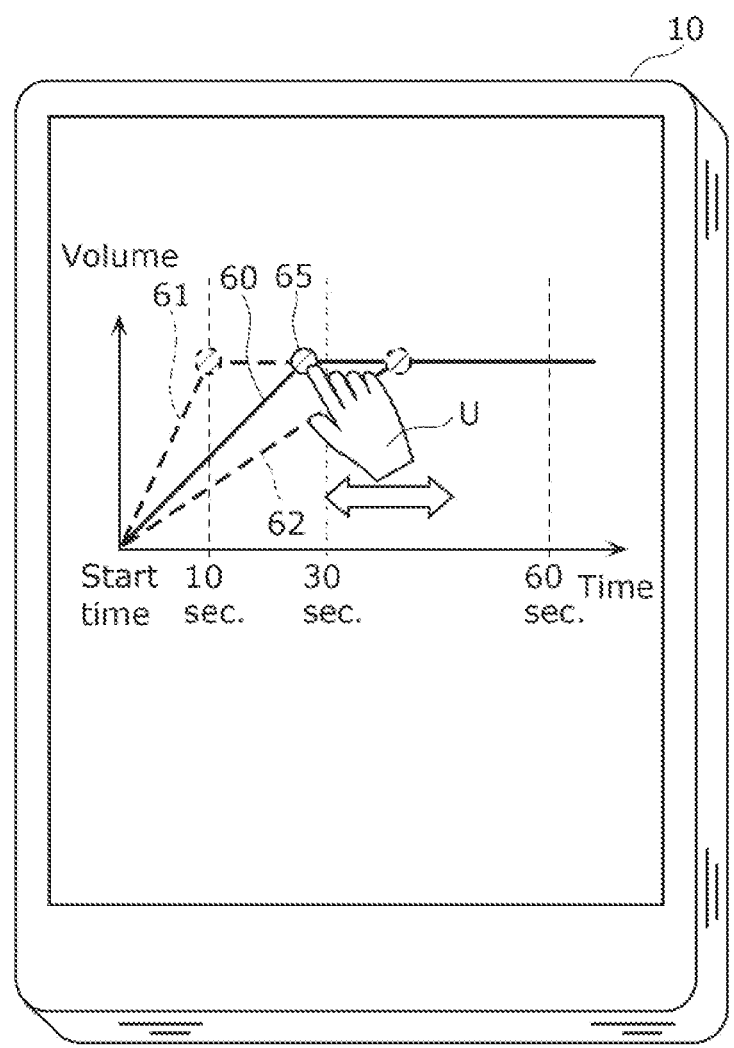
FIG. 9 is a descriptive diagram illustrating an image for a pattern adjustment operation according to the embodiment.

FIG. 9 is a descriptive diagram illustrating a method for adjusting the pattern according to the present embodiment.

FIG. 9 illustrates terminal 10 displaying an image for adjusting the pattern. These descriptions assume that the display screen of terminal 10 is a touch panel display and can accept touch operations made by user U, but the mode of operation is not limited thereto.

Terminal 10 displays, in the display screen, an image showing pattern 60 generated based on the initial pattern in step S103. The displayed image shows the timewise change in volume, with the horizontal axis representing time and the vertical axis representing the volume of the alarm. The displayed image also shows operation point 65, which indicates the location where an operation by user U is accepted.

Terminal 10 also accepts operations to extent and contract the displayed pattern in the time direction through a touch operation made by user U on the screen. Once the stated operation is accepted, terminal 10 updates the displayed image to an image that extended in the time direction. User U is expected to manipulate operation point 65 to reflect their own wishes.

For example, if user U makes a touch operation for contracting the pattern (an operation of moving the point to the left in the drawing), terminal 10 updates pattern 60 to pattern 61 that is contracted in the time direction. If user U makes a touch operation for extending the pattern (an operation of moving the point to the right in the drawing), terminal 10 updates pattern 60 to pattern 62 that is extended in the time direction.

In this manner, system 1 can control the output of the alarm sound using pattern 61 or 62, which reflect the wishes of user U with respect to pattern 60 generated based on the initial pattern.

Note that the plurality of users may include users who do not use the adjustment function illustrated in FIG. 9.

In this case, the processing of step S103 makes it possible to distribute the speed of the increase in the volume of the alarm sound among the terminals operated by users who did not use the adjustment function.

As a result, the wakeup times are distributed among the plurality of users, and the times when users perform the operation to stop the output of the alarm sound output are distributed as well, and thus the times for requesting the presentation information from server 20 are also distributed.

According to this action, system 1 according to the present embodiment provides an effect of reducing the concentration of the load on server 20 even when there are a plurality of users who do not use the adjustment function illustrated in FIG. 9.

Figure 10:
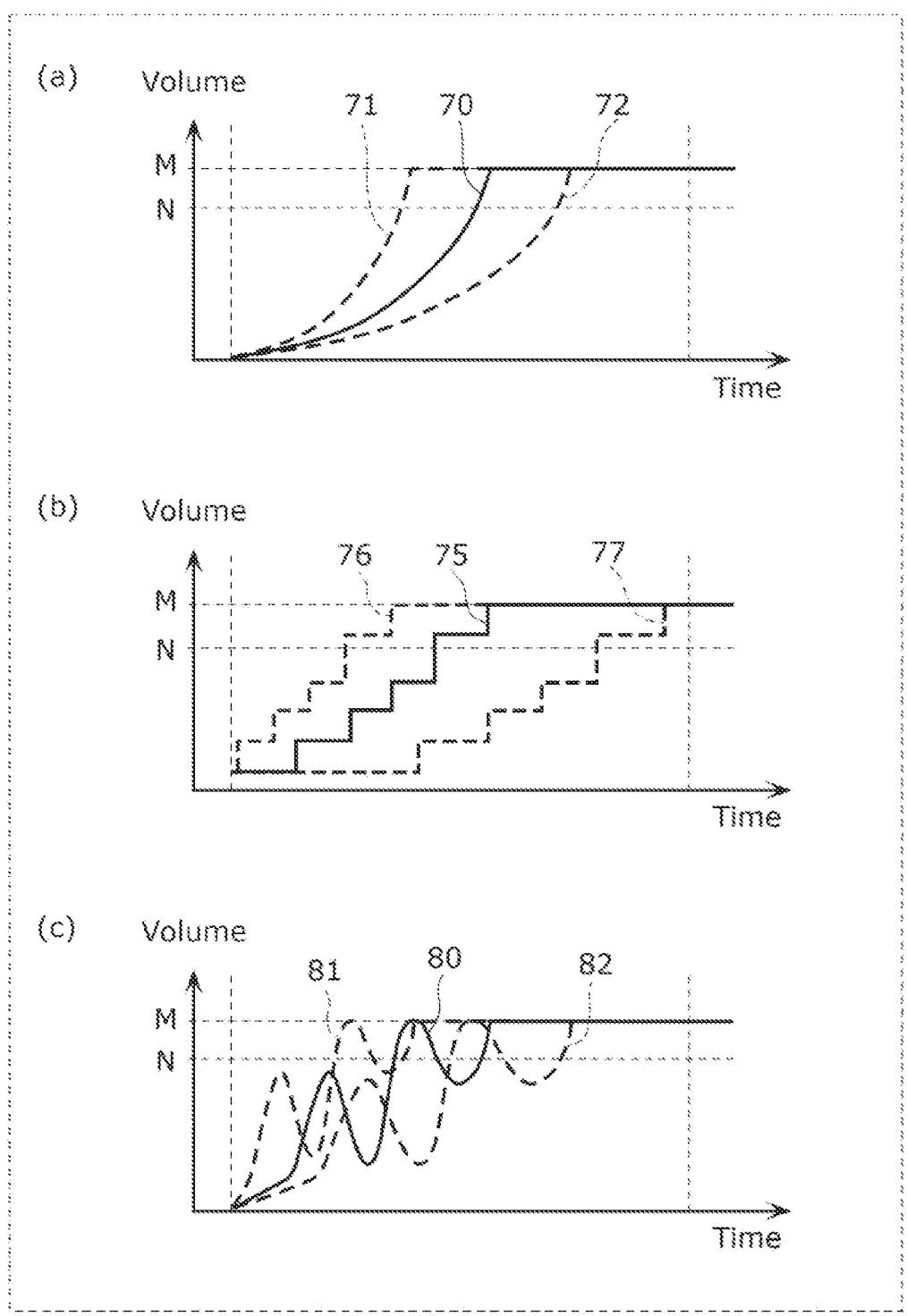
FIG. 10 is a descriptive diagram illustrating an example of an initial pattern according to the embodiment.

FIG. 10 is a descriptive diagram illustrating an example of the initial pattern according to the present embodiment.

Initial pattern 70 illustrated in (a) in FIG. 10 is an example of the initial pattern in which the volume increases along a curve as time passes from the start time, reaches the maximum volume, and then stays at the maximum volume thereafter. The curve may have any shape. Patterns 71 and 72 illustrated in (a) in FIG. 10 are examples of contracted and extended patterns of initial pattern 70, respectively.

Initial pattern 75 illustrated in (b) of FIG. 10 is an example of the initial pattern in which the volume increases in steps as time passes from the start time, reaches the maximum volume, and then stays at the maximum volume thereafter. Each step may increase by any amount. Patterns 76 and 77 illustrated in (b) of FIG. 10 are examples of contracted and extended patterns of initial pattern 75, respectively.

Initial pattern 80 illustrated in (c) of FIG. 10 is an example of the initial pattern in which the volume repeatedly increases or decreases along curves as time passes from the start time, reaches the maximum volume, and then stays at the maximum volume thereafter. The curves may have any shape. It is also possible to reach the maximum volume temporarily when the volume is repeatedly increasing or decreasing. Patterns 81 and 82 illustrated in (c) of FIG. 10 are examples of contracted and extended patterns of initial pattern 80, respectively.

By using initial patterns 70, 75 and 80 illustrated in (a), (b), and (c) of FIG. 10, the intensity of the stimulus can be varied flexibly in various patterns to prompt user U to wake up.

Variation 1 on the Embodiment

The present variation will describe another application of the configuration of the system for suppressing an increase in the load on the server. In the present variation, an example of application in a system that remotely controls an apparatus or a device in a user's home from a device outside the home will be described. Here, an example of application in a control system that controls the filling of a bathtub as the apparatus or device in the user's home will be described.

Figure 11:
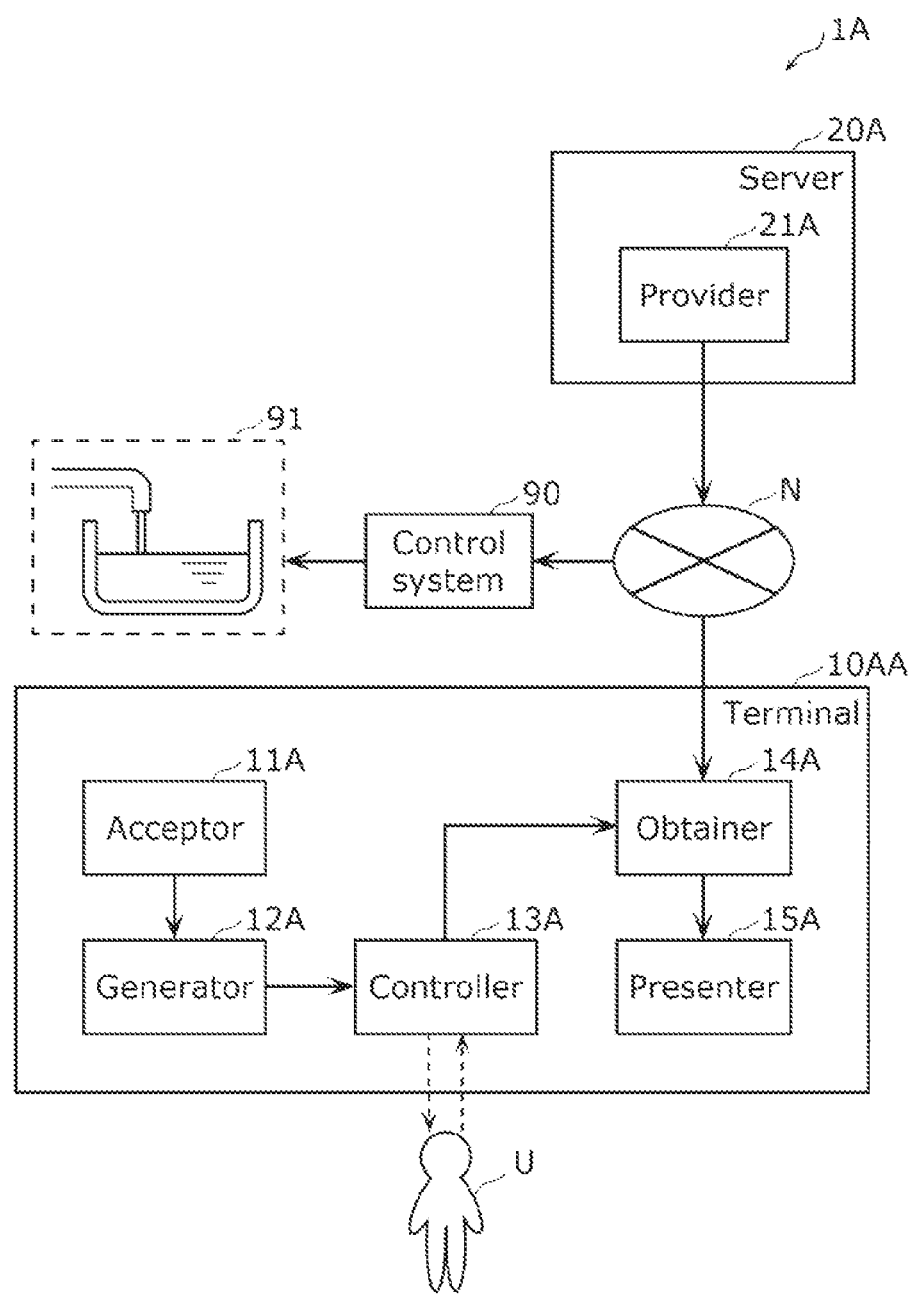
FIG. 11 is a descriptive diagram schematically illustrating the configuration of a system according to Variation 1 on the embodiment.

FIG. 11 is a descriptive diagram schematically illustrating the configuration of system 1A according to the present variation.

As illustrated in FIG. 11, system 1A includes terminal 10AA, server 20A, and control system 90. Terminal 10AA, server 20A, and control system 90 are communicably connected over network N.

Terminal 10AA is a communication terminal owned by user U. Terminal 10AA accepts a fill time for bathtub 91 and a notice time from user U. The "fill time" is a scheduled time to start filling bathtub 91 with hot water, and the "notice time" is a time to inquire with user U as to whether or not to start filling bathtub 91 with hot water at the fill time as scheduled. When the notice time arrives, terminal 10AA presents information to user U inquiring whether or not to fill bathtub 91 with hot water as scheduled. Terminal 10AA also obtains information indicating the user's response to the inquiry (also called "response information") and provides that information to server 20A if the response is affirmative. When terminal 10AA presents the stated inquiry information to user U, a stimulus such as sound or vibration is used to make user U aware of the presentation.

Server 20A is a server that controls the filling of bathtub 91 with hot water. Server 20A includes provider 21A that provides information to be provided to terminal 10AA and control system 90.

Provider 21A obtains the response information from terminal 10AA indicating the response to the inquiry to user U. If the response information is an affirmative response, i.e., a response indicating that filling is to be performed at the fill time as scheduled, information for controlling the filling of bathtub 91 with hot water (also called "control information") is provided by transmitting that information to control system 90.

Control system 90 is a control system that controls the filling of bathtub 91 with hot water. Control system 90 fills bathtub 91 with hot water when the control information for performing the filling is obtained from server 20A.

Terminal 10AA will be described in further detail. Of the function units included in terminal 10AA, those that are the same as those in terminal 10 of the foregoing embodiment will not be described in detail.

As illustrated in FIG. 11, terminal 10AA includes acceptor 11A, generator 12A, controller 13A, obtainer 14A, and presenter 15A. The function units of terminal 10AA can be realized by a CPU executing programs using memory.

Acceptor 11A is a function unit that accepts the fill time and the notice time. The processing by which acceptor 11A accepts the fill time and the notice time is the same as the processing by which acceptor 11 of the foregoing embodiment receives the start time. The fill time is an example of the stimulus start time, which is a time at which the output of a stimulus is to be started.

Generator 12A is a processing unit that generates a pattern indicating a timewise change in the intensity of the stimulus (also called simply a "pattern"). The processing by which generator 12A generates the pattern indicating the timewise change in the intensity of the stimulus is the same as the processing by which generator 12 of the foregoing embodiment generates a pattern indicating the timewise change in the volume of the alarm sound.

Controller 13A is a processing unit that controls the output of a stimulus by terminal 10AA. Controller 13A performs control for starting the output of the stimulus at the notice time and outputting the stimulus at the intensity indicated by the pattern generated by generator 12A. The stimulus output by controller 13A can be sound, vibration, light, an image, or the like, which can be output by a speaker, a motor, a light source, or a display screen (not shown) provided in terminal 10AA, respectively. Additionally, when an operation for stopping the output of the stimulus is received from user U, controller 13A performs control for stopping the output of the stimulus. The processing by which controller 13A controls the output of the stimulus by terminal 10AA is the same as the processing by which controller 13 controls the output of the alarm sound in the embodiment.

Obtainer 14A is a processing unit that obtains the presentation information from server 20A. Upon receiving a response to an inquiry to user U from user U, obtainer 14A transmits the response information indicating the response to server 20A. Then, obtainer 14A obtains the presentation information transmitted by server 20A in response to the request. The presentation information includes information indicating that a response has been received from user U.

Presenter 15A is a processing unit that presents the presentation information to user U. Presenter 15A presents the presentation information obtained by obtainer 14A to the user using the UI device. Specifically, presenter 15A presents the presentation information to user U by displaying the information in a screen serving as the UI device or outputting the information as audio using a speaker serving as the UI device.

Figure 12:
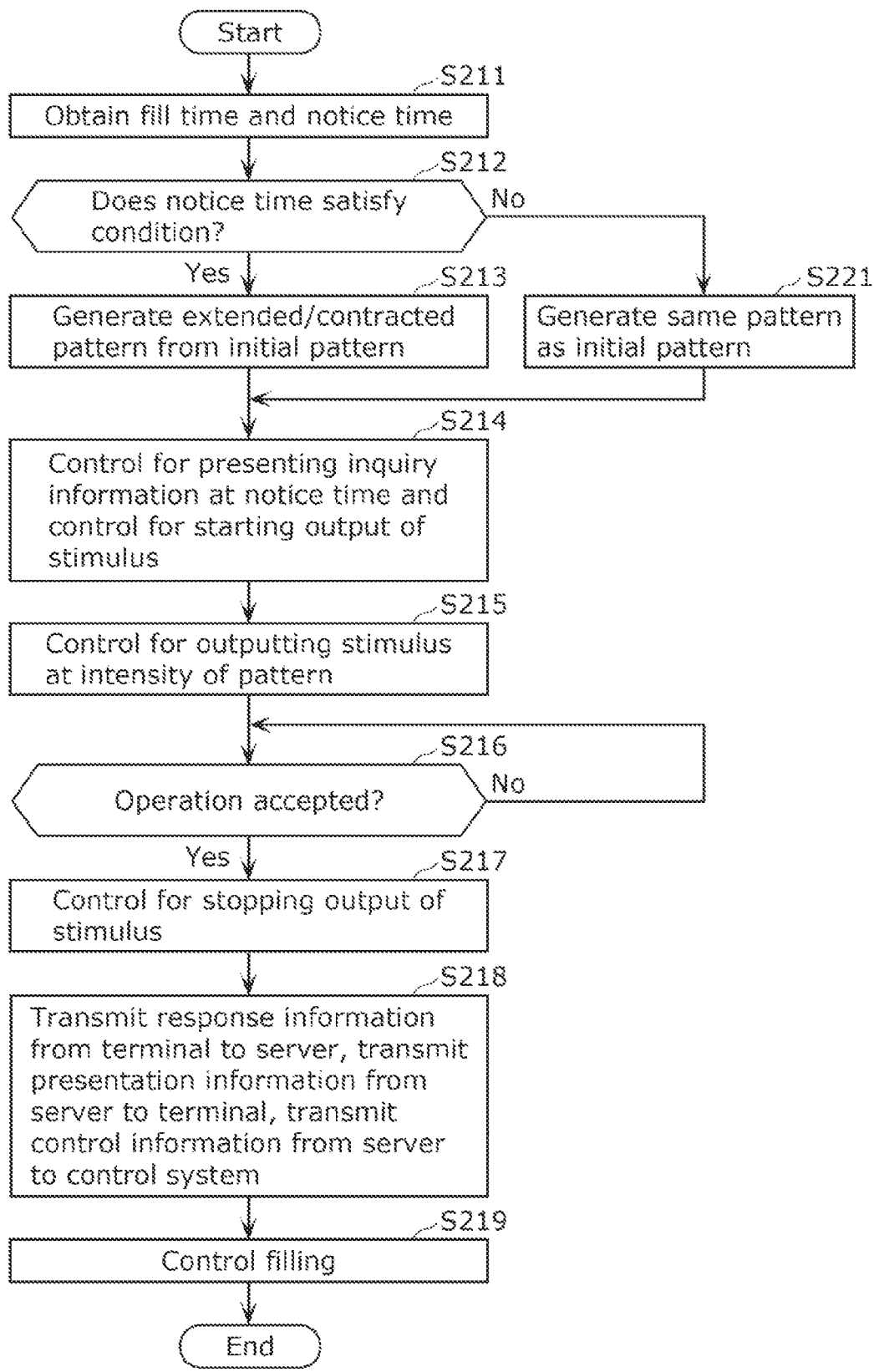
FIG. 12 is a flowchart illustrating processing executed by the system according to Variation 1 on the embodiment.

FIG. 12 is a flowchart illustrating processing executed by system 1A according to the present variation. The flowchart in FIG. 12 illustrates a control method for controlling a device that outputs a stimulus to a user.

In step S211, acceptor 11A obtains the fill time and the notice time from user U.

In step S212, generator 12A determines whether or not the notice time accepted by acceptor 11A in step S211 satisfies a predetermined condition. More specifically, generator 12A determines whether or not the notice time accepted by acceptor 11A in step S211 is a time set in advance as a time having a good timing, e.g., whether the minute numerical value of the notice time matches one of "0, 30, 15, 45, 10, 20, 40, or 50". If the notice time satisfies the predetermined condition (Yes in step S212), the sequence moves to step S213, and if not (No in step S212), the sequence moves to step S221.

In step S213, generator 12A generates an extended pattern from the initial pattern. At this time, generator 12A may set a different extension/contraction rate according to the minute numerical value of the start time, and then generate an extended pattern using the set extension/contraction rate.

In step S221, generator 12A generates the same pattern as the initial pattern.

After the processing of step S213 or step S221 ends, the sequence moves to step S214.

In step S214, controller 13A performs control for presenting inquiry information and starting the output of the stimulus at the notice time based on control of server 20A.

In step S215, controller 13A controls the output of the stimulus at the intensity indicated by the pattern determined in step S213. It is assumed the stimulus output in this manner will cause user U to notice the inquiry as to whether or not bathtub 91 is to be filled at the fill time as scheduled, and to operate terminal 10AA to stop outputting the stimulus.

In step S216, controller 13A determines whether or not an operation of inputting the response information indicating the response of user U to the inquiry information presented in step S214, and an operation of stopping the output of the stimulus, have been accepted. If it is determined that the operations have been accepted (Yes in step S216), the sequence moves to step S217, and if not (No in step S216), step S216 is executed again. In other words, controller 13A enters a standby state in step S216 until the operations are accepted.

In step S217, controller 13A performs control for stopping the output of the stimulus.

In step S218, terminal 10AA transmits the response information to server 20A. In addition, server 20A transmits the presentation information to terminal 10AA and transmits the control information to control system 90. At this time, server 20A executes communication processing involved with communication with terminal 10AA and control system 90, and generation processing for generating the presentation information and the control information.

In step S219, control system 90 controls the filling of bathtub 91 with hot water based on the control information obtained from server 20A.

Note that the timing of the processing of step S213 and step S221 is the same as the timing of the processing of step S103 and step S111 in the foregoing embodiment.

The sequence of processing illustrated in FIG. 12 makes it possible for system 1A to suppress an increase in the load on server 20A. Specifically, an increase in the load on server 20A can be suppressed by distributing the timings of the communication processing and generation processing performed by server 20A when step S218 is being executed.

Variation 2 on the Embodiment

The present variation will describe another application of the configuration of the system for suppressing an increase in the load on the server. In the present variation, an example of application in a system that remotely controls an apparatus or a device in a user's home from a device outside the home will be described. Here, an example of application in a playback system that plays back a moving image stored in an image recording device as the apparatus or device in the user's home will be described.

Figure 13:
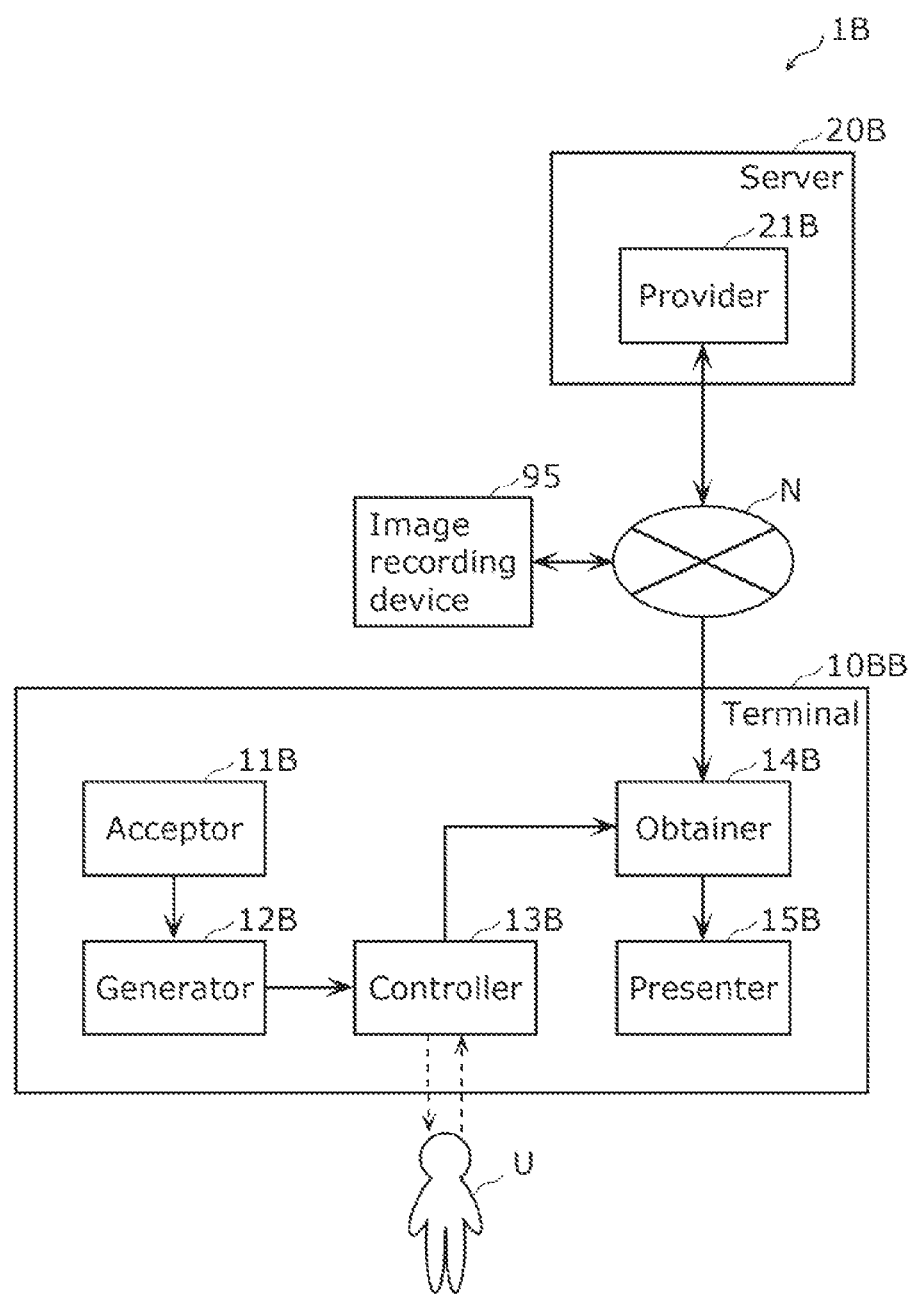
FIG. 13 is a descriptive diagram schematically illustrating the configuration of a system according to Variation 2 on the embodiment.

FIG. 13 is a descriptive diagram schematically illustrating the configuration of system 1B according to the present variation.

As illustrated in FIG. 13, system 1B includes terminal 10BB, server 20B, and image recording device 95. Terminal 10BB, server 20B, and image recording device 95 are communicably connected over network N. In general, the IP addresses used by terminal 10BB and image recording device 95 for communication are assigned dynamically, for example, by Dynamic Host Configuration Protocol (DHCP). The IP address that server 20B uses for communication is statically assigned. Therefore, it is not expected that terminal 10BB and image recording device 95 will communicate directly with each other, but will instead use relay facilitated by server 20B.

Terminal 10BB is a communication terminal owned by user U. Terminal 10BB accepts a playback time from user U. The playback time is a time when the playback of a moving image stored in image recording device 95 is scheduled to start. When the playback time arrives, terminal 10BB presents user U with information inquiring whether or not to start playing back the moving image as scheduled. Terminal 10BB also obtains information indicating the user's response to the inquiry (also called "response information") and provides that information to server 20B. When terminal 10BB presents the stated inquiry information to user U, a stimulus such as sound or vibration is used to make user U aware of the presentation.

Server 20B is a server that controls the operations of image recording device 95. Server 20B includes provider 21B that provides information to be provided to terminal 10BB and image recording device 95.

Provider 21B obtains the response information from terminal 10BB indicating the response to the inquiry to user U. If the response information is an affirmative response, i.e., a response indicating that the moving image is to be played back as scheduled, information for transmitting moving image data to terminal 10BB (also called "control information") is provided by transmitting that information to image recording device 95. Additionally, provider 21B receives the moving image data from image recording device 95 and provides the moving image data by transmitting the data to terminal 10BB.

Image recording device 95 is a device that records broadcast data received from outside by storing the data, and plays back the recorded broadcast data. Image recording device 95 transmits recorded data to terminal 10BB via server 20B based on instructions from server 20B. When playback starts, the first few minutes of data are transmitted at once, which increases the load on image recording device 95 and server 20B for data processing and communication processing, and increases the amount of communication.

Terminal 10BB will be described in further detail. Of the function units included in terminal 10BB, those that are the same as those in the foregoing embodiment will not be described in detail.

As illustrated in FIG. 13, terminal 10BB includes acceptor 11B, generator 12B, controller 13B, obtainer 14B, and presenter 15B. The function units of terminal 10BB can be realized by a CPU executing programs using memory.

Acceptor 11B is a function unit that accepts the playback time. The processing by which acceptor 11B accepts the playback time is the same as the processing by which acceptor 11 of the foregoing embodiment receives the start time. The playback time is an example of a stimulus start time, which is a time at which the output of a stimulus is to be started.

Generator 12B is a processing unit that generates a pattern indicating a timewise change in the intensity of the stimulus (also called simply a "pattern"). The processing by which generator 12B generates the pattern indicating the timewise change in the intensity of the stimulus is the same as the processing by which generator 12 of the foregoing embodiment generates a pattern indicating the timewise change in the volume of the alarm sound.

Controller 13B is a processing unit that controls the output of a stimulus by terminal 10BB. Controller 13B performs control for starting the output of the stimulus at the playback time and outputting the stimulus at the intensity indicated by the pattern generated by generator 12B. The stimulus output by controller 13B can be sound, vibration, light, an image, or the like, which can be output by a speaker, a motor, a light source, or a display screen (not shown) provided in terminal 10BB, respectively. Additionally, when an operation for stopping the output of the stimulus is received from user U, controller 13B performs control for stopping the output of the stimulus. The processing by which controller 13B controls the output of the stimulus by terminal 10BB is the same as the processing by which controller 13 controls the output of the alarm sound in the embodiment.

Obtainer 14B is a processing unit that obtains the moving image data from image recording device 95 via server 20B. Obtainer 14B transmits response information to server 20B upon when an operation is accepted from user U to stop the output of the stimulus. Obtainer 14B receives and obtains the moving image data transmitted from image recording device 95 via server 20B by server 20B controlling image recording device 95 in accordance with the response information.

Presenter 15B is a processing unit that presents the moving image to user U. Presenter 15B presents the moving image in the moving image data obtained by obtainer 14B to the user using the UI device. Specifically, presenter 15B presents the moving image to user U by displaying the information in a screen serving as the UI device or outputting the information as audio using a speaker serving as the UI device.

Figure 14:
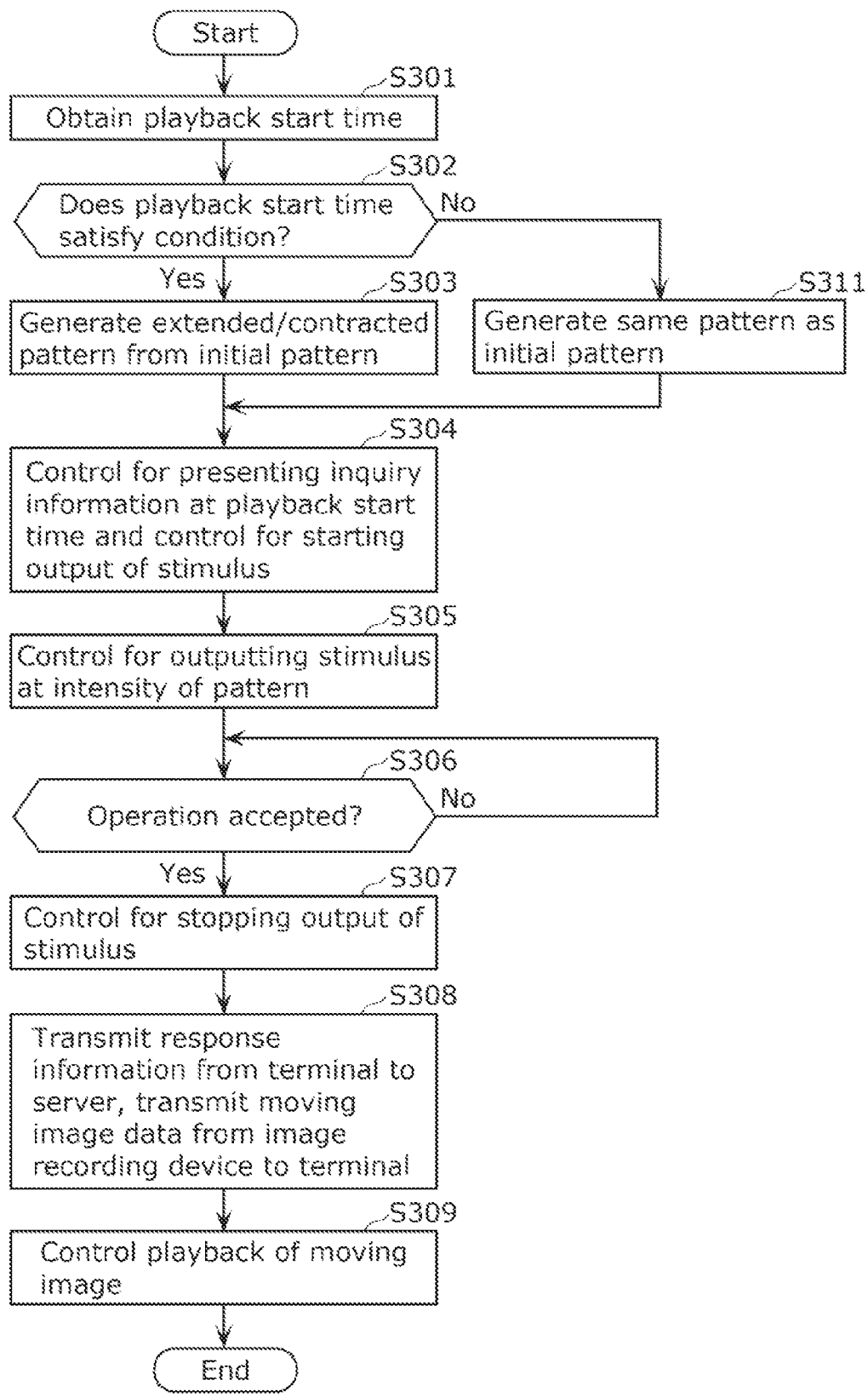
FIG. 14 is a flowchart illustrating processing executed by the system according to Variation 2 on the embodiment.

FIG. 14 is a flowchart illustrating processing executed by system 1B according to the present variation. The flowchart in FIG. 14 illustrates a control method for controlling a device that outputs a stimulus to a user.

In step S301, acceptor 11B obtains the playback time from user U.

In step S302, generator 12B determines whether or not the playback time accepted by acceptor 11B in step S301 satisfies a predetermined condition. More specifically, generator 12B determines whether or not the playback time accepted by acceptor 11B in step S301 is a time set in advance as a time having a good timing, e.g., whether the minute numerical value of the playback time matches one of "0, 30, 15, 45, 10, 20, 40, or 50". If the playback time satisfies the predetermined condition (Yes in step S302), the sequence moves to step S303, and if not (No in step S302), the sequence moves to step S311.

In step S303, generator 12B generates an extended pattern from the initial pattern. At this time, generator 12B may set a different extension/contraction rate according to the minute numerical value of the start time, and then generate an extended pattern using the set extension/contraction rate.

In step S311, generator 12B generates the same pattern as the initial pattern.

After the processing of step S303 or step S311 ends, the sequence moves to step S304.

In step S304, controller 13B performs control for presenting inquiry information and starting the output of the stimulus at the playback time based on control of server 20B.

In step S305, controller 13B controls the output of the stimulus at the intensity indicated by the pattern determined in step S303. It is assumed the stimulus output in this manner will cause user U to notice the inquiry as to whether or not to play back the moving image at the playback time as scheduled, and to operate terminal 10BB to stop outputting the stimulus.

In step S306, controller 13B determines whether or not an operation of inputting the response information indicating the response of user U to the inquiry information presented in step S304, and an operation of stopping the output of the stimulus, have been accepted. If it is determined that the operations have been accepted (Yes in step S306), the sequence moves to step S307, and if not (No in step S306), step S306 is executed again. In other words, controller 13B enters a standby state in step S306 until the operations are accepted.

In step S307, controller 13B performs control for stopping the output of the stimulus.

In step S308, terminal 10BB transmits the response information to server 20B. Server 20B causes the moving image data to be transmitted to terminal 10BB from image recording device 95 via server 20B by transmitting control information to image recording device 95.

At this time, server 20B executes communication processing for communicating with terminal 10BB and image recording device 95, respectively.

In step S309, terminal 10BB controls the playback of the moving image using the moving image data received from image recording device 95 via server 20B.

Note that the timing of the processing of step S303 and step S311 is the same as the timing of the processing of step S103 and step S111 in the foregoing embodiment.

The sequence of processing illustrated in FIG. 14 makes it possible for system 1B to suppress an increase in the load on server 20B. Specifically, an increase in the load on server 20B can be suppressed by distributing the timings of the communication processing and generation processing performed by server 20B when step S308 is being executed.

Variation 3 on the Embodiment

The present variation will describe another example of the configuration of the system for suppressing an increase in the load on the server.

The same reference signs may be used for the same constituent elements as those in the foregoing embodiment, and detailed descriptions thereof may be omitted.

Figure 15:
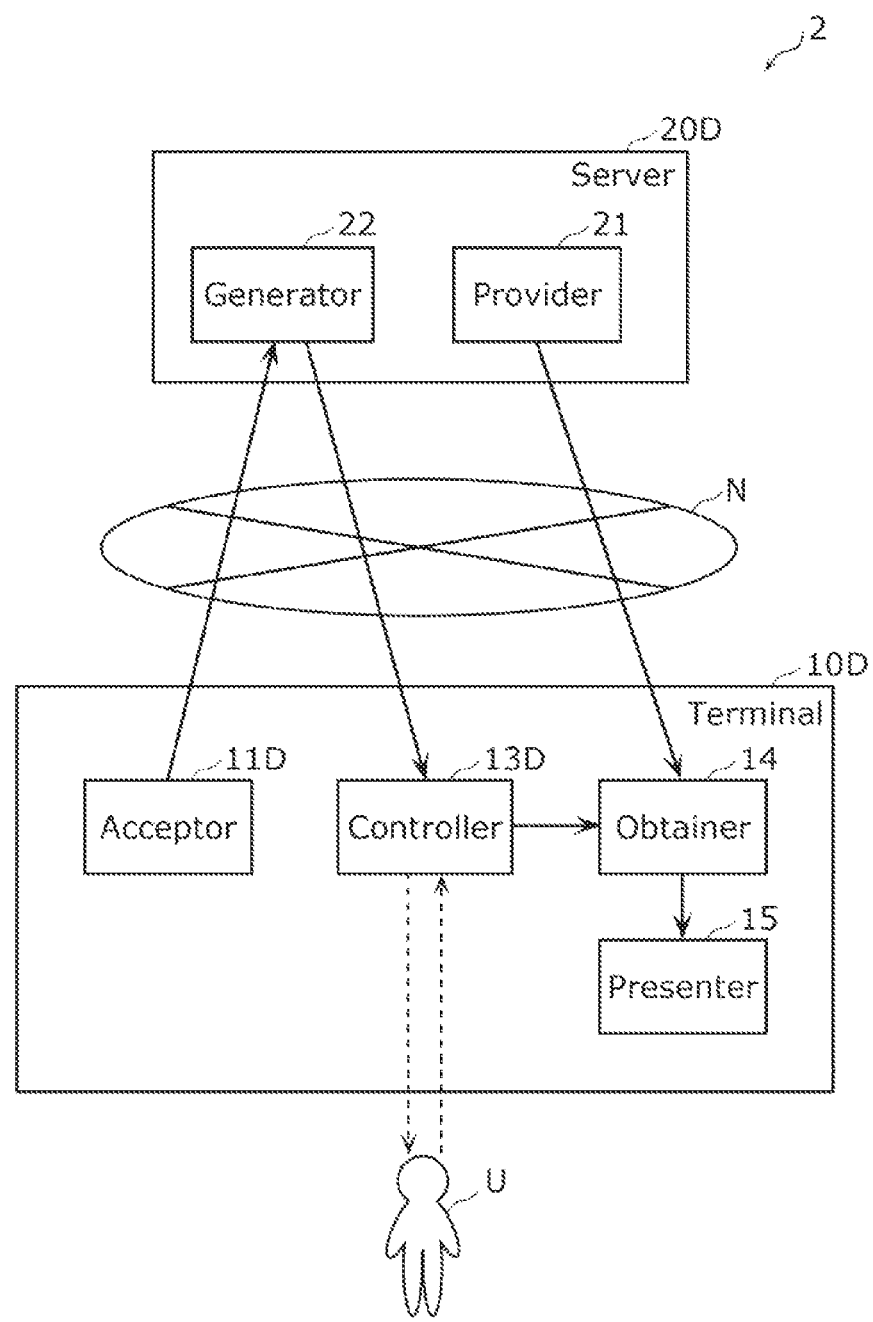
FIG. 15 is a descriptive diagram schematically illustrating the configuration of a system according to Variation 3 on the embodiment.

FIG. 15 is a descriptive diagram schematically illustrating the configuration of system 2 according to the present variation.

System 2 according to the present variation includes terminal 10D and server 20D.

Terminal 10D includes acceptor 11D, controller 13D, obtainer 14, and presenter 15.

Server 20D includes provider 21 and generator 22.

System 2 differs from system 1 in the foregoing embodiment mainly in that server 20D includes generator 22.

Acceptor 11D is a processing unit that accepts the start time, which is the time when terminal 10D is to start outputting the alarm sound. Upon accepting the start time, acceptor 11D transmits the accepted start time to generator 22 of server 20D. Other aspects of acceptor 11D are the same as acceptor 11 in the foregoing embodiment.

Generator 22 is a processing unit that generates a pattern of the alarm sound. Generator 22 receives the start time from acceptor 11D of terminal 10D, generates an alarm sound pattern using the received start time, and transmits the generated pattern to terminal 10D. Other aspects of generator 22 are the same as generator 12 in the foregoing embodiment.

Controller 13D is a processing unit that controls the output of the alarm sound by terminal 10D. Controller 13D receives the pattern from generator 22 of server 20D and controls the output of an alarm according to the received pattern. Other aspects of controller 13D are the same as controller 13 in the foregoing embodiment.

With system 2 according to the present variation, the pattern generation processing by generator 22 is performed by server 20D, which provides an effect of reducing the work and power consumption related to the maintenance of a program for the generation processing. For example, when updating the program for the generation processing, if the pattern generation processing is executed by a plurality of terminals 10 as in system 1, each of the plurality of terminals 10 must download the program in advance, and the downloading requires work and consumes power. In contrast, when server 20D executes the pattern generation processing as in system 2, there is a benefit in that the work and power consumption involved in the downloading of the program is reduced.

Variation 4 on the Embodiment

The present variation will describe another example of the configuration of the system for suppressing an increase in the load on the server.

The same reference signs may be used for the same constituent elements as those in the foregoing embodiment or variations, and detailed descriptions thereof may be omitted.

Figure 16:
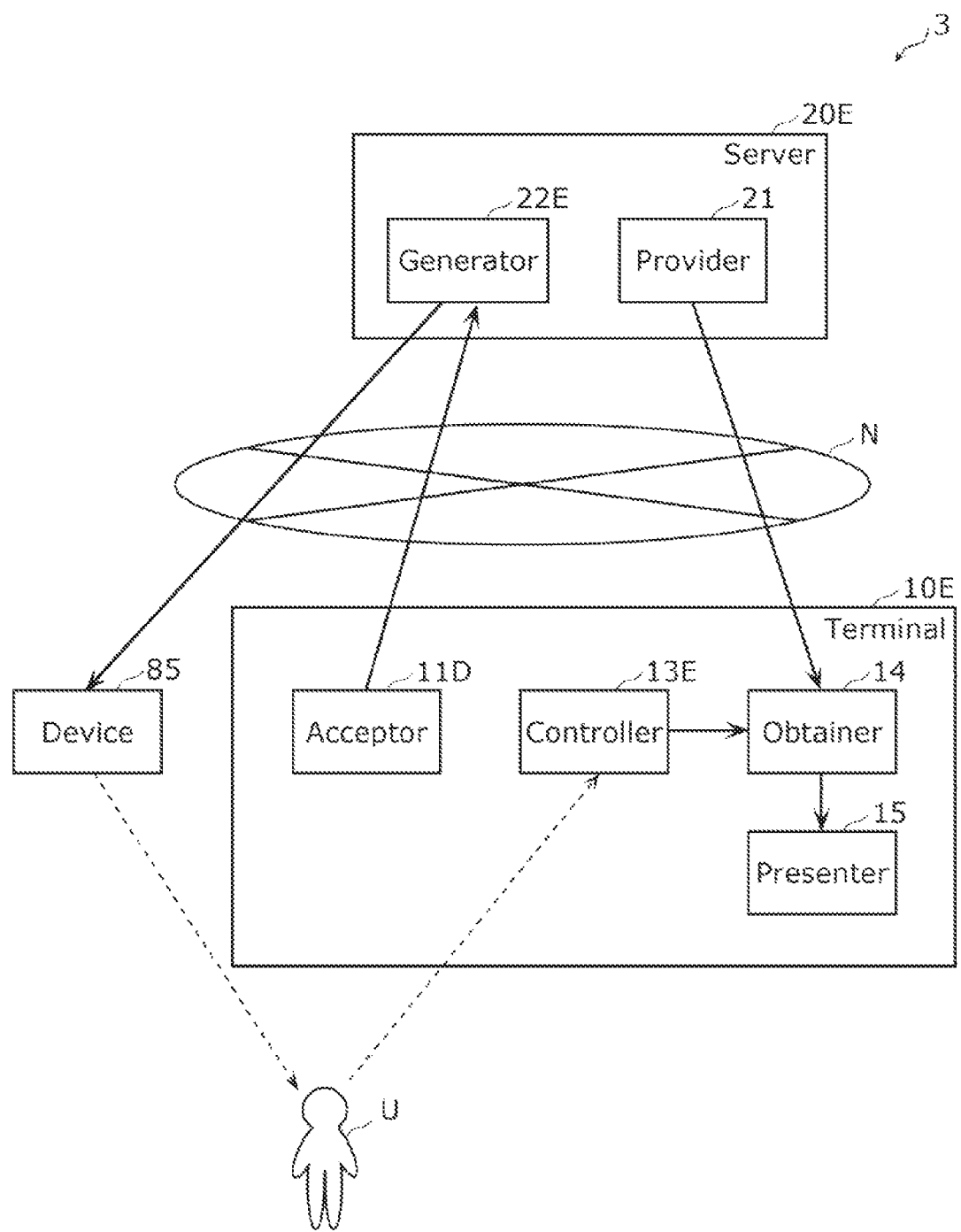
FIG. 16 is a descriptive diagram schematically illustrating the configuration of a system according to Variation 4 on the embodiment.

FIG. 16 is a descriptive diagram schematically illustrating the configuration of system 3 according to the present variation.

System 3 according to the present variation includes terminal 10E, server 20E, and device 85.

Terminal 10E includes acceptor 11D, controller 13E, obtainer 14, and presenter 15.

Server 20E includes provider 21 and generator 22E.

System 3 differs from system 2 in the foregoing Variation 3 mainly in that of the functions of controller 13D, the function of outputting the stimulus is provided in device 85.

Generator 22E is a processing unit that generates a pattern of the alarm sound. Generator 22E receives the start time from acceptor 11D of terminal 10E, generates an alarm sound pattern using the received start time, and transmits the generated pattern to device 85. Other aspects of generator 22E are the same as generator 12 in the foregoing embodiment.

Device 85 is a device that outputs the alarm sound, e.g., a speaker device. Device 85 receives the pattern from generator 22E of server 20E and controls the output of the alarm sound according to the received pattern. Other aspects of device 85 are the same as controller 13 in the foregoing embodiment. Device 85 may be an air conditioner or fan that outputs wind as the stimulus, a lighting device that outputs light as the stimulus, a mobile terminal or bedding that outputs vibration as the stimulus, or the like. Device 85 may be a dedicated device for outputting the stimulus to user U, or a device used by user U in their daily life may also function as device 85.

Additionally, when an operation for stopping the alarm sound is received from user U, controller 13E performs control for stopping the output of the alarm sound.

Note that the stimulus output by device 85 may include not only an alarm sound, as described in the foregoing embodiment, but may also more generally include sound, light, temperature, wind, or vibration, and may include the presence or absence, or changes in the intensity, of any of these.

A case where device 85 is a lighting device, and a stimulus is output using light, will be described in detail as an example.

Figure 17:
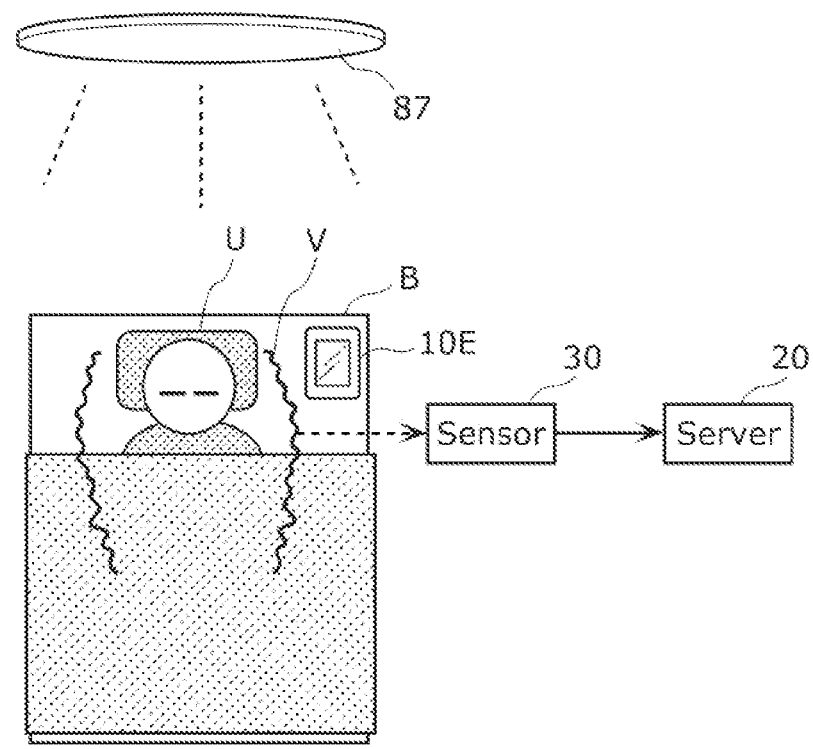
FIG. 17 is a descriptive diagram illustrating a usage example of the system according to Variation 4 on the embodiment.
Figure 18:
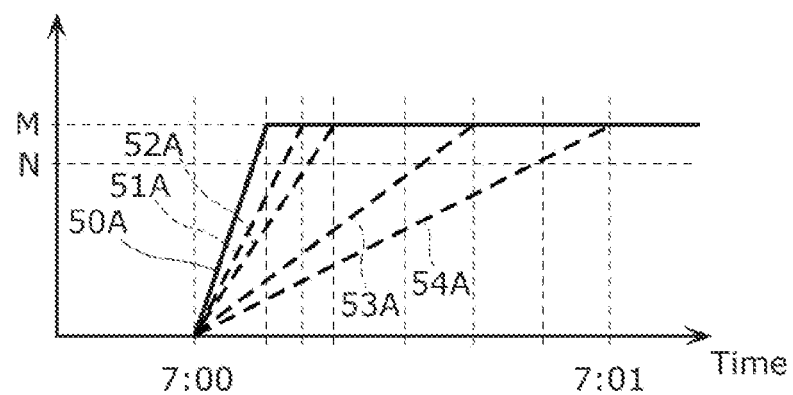
FIG. 18 is a descriptive diagram of an extension/contraction rate range according to Variation 4 on the embodiment.

FIG. 17 is a descriptive diagram illustrating a usage example of the system according to the present variation. FIG. 18 is a descriptive diagram of an extension/contraction rate range according to the present variation.

In FIG. 17, lighting device 87 is illustrated as an example of device 85. Other aspects are the same as the usage example of the system according to the foregoing embodiment (see FIG. 2).

Lighting device 87 is a ceiling light mounted on the ceiling of the sleeping user U's room. As lighting device 87, it is also possible to use a lighting device attached to a structural material such as the ceiling, wall, or floor of user U's room, or a portable lighting device placed in user U's room.

In this case, generator 22E generates a pattern of light intensity output by lighting device 87. The pattern of light intensity generated is illustrated in FIG. 18. FIG. 18 illustrates the pattern of the volume of the alarm sound (see FIG. 5) in the embodiment as a pattern of light intensity.

As illustrated in FIG. 18, the horizontal axis represents time and the vertical axis represents the intensity of the light, and patterns 50A, 51A, 52A, 53A, and 54A are shown for the timewise change in the intensity. Intensity MA on the vertical axis indicates a maximum intensity, and intensity NA is 70 to 80% of the maximum intensity, indicating the intensity of light at which user U is expected to wake up.

Patterns 50A, 51A, 52A, 53A, and 54A of the timewise change in the intensity are the same as patterns 50, 51, 52, 53, and 54 of the timewise change in the volume of the alarm sound in the embodiment, respectively, and will therefore not be described in detail.

Lighting device 87 adjusts the intensity of the output light according to the pattern generated by generator 22E.

With system 3 according to the present variation, user U can be given a stimulus output by various devices, such as dedicated devices or devices used in their daily life. In particular, giving user U a stimulus using a device they use in their daily life has an advantage in that no dedicated device need be used.

As described thus far, with the control method according to the foregoing embodiment and variations, when the stimulus start time obtained from the user satisfies the predetermined condition, the stimulus is output in a pattern extended or contracted from the initial pattern, and thus the timing of the user's activity based on the output stimulus (specifically, waking up) can be distributed over time. Then, when the server executes processing based on the user's activity, the timing of the processing executed by the server can be distributed, which makes it possible to suppress an increase in the load on the server. In this manner, the control method according to the present disclosure makes it possible to suppress an increase in the load on the server.

Additionally, the timing of the processing executed by the server can be distributed when a time having a relatively high probability of being set as the stimulus start time by a plurality of users is set. A time having a relatively high probability of being set as the stimulus start time by a plurality of users can be set as the stimulus start time by many users. This makes it easy for the load on the server to increase at that time. Accordingly, when the stimulus start time obtained from the user is a time having a relatively high probability of being set as the stimulus start time by a plurality of users, outputting the stimulus in a pattern extended from the initial pattern makes it possible to distribute the timing of the processing executed by the server. In this manner, the control method according to the present disclosure makes it possible to suppress an increase in the load on the server.

Additionally, a time in which, specifically, the numerical value of the unit of minutes, when the time is expressed in hour/minute/second format, is an integral multiple of 0 or 10, or an integral multiple of 15, is used as the time having a relatively high probability of being set as the stimulus start time by a plurality of users, and thus whether or not the time has a relatively high probability of being set as the stimulus start time by a plurality of users can be determined more easily. In this manner, the control method according to the present disclosure makes it possible to suppress an increase in the load on the server more easily.

Additionally, when the time has a relatively high probability of being set as the stimulus start time by a plurality of users, the pattern is generated in accordance with the numerical value of the unit of minutes. A pattern extended using a higher extension/contraction rate is generated as the probability increases. Accordingly, the extension/contraction rate of the pattern increases as times for the stimulus start time are set which are likely to increase the load on the server, and the effect of distributing the load on the server can be increased. In this manner, the control method according to the present disclosure makes it possible to suppress an increase in the load on the server adaptively in accordance with the stimulus start time which has been set.

Additionally, the pattern is generated using an extension/contraction rate which has been selected at random from the set extension/contraction rate range, which makes it possible to increase the effect of distributing the load on the server. As such, the control method according to the present disclosure makes it possible to further suppress an increase in the load on the server.

Additionally, a pattern in which the intensity of the stimulus stays constant or increases as time passes is used as the initial pattern, and the stimulus is output to the user using a pattern generated from the initial pattern. Accordingly, the control method according to the present disclosure makes it possible to suppress an increase in the load on the server more easily.

Additionally, a pattern that ultimately stimulates the user at a maximum intensity after increasing or decreasing partway through is used as the initial pattern, and the stimulus is output to the user using a pattern generated from the initial pattern. Accordingly, the control method according to the present disclosure makes it possible to suppress an increase in the load on the server more easily.

Additionally, an increase in the load caused by communication processing and processing for generating the presentation information, executed by the server after accepting an operation from the user, is suppressed. As such, the control method according to the present disclosure makes it possible to suppress an increase in the load from processing including the communication processing and generation processing performed by the server.

Additionally, processing performed by the server for outputting a stimulus prompting the user to wake up and presenting presentation information to the user who has woken up based on the output stimulus can be distributed over time. As such, the control method according to the present disclosure makes it possible to suppress an increase in the load on the server.

Additionally, any one of sound, light, temperature, wind, or vibration is used as the stimulus. Accordingly, the control method according to the present disclosure can suppress an increase in the load on the server while using any one of sound, light, temperature, wind, or vibration as the stimulus.

The foregoing embodiments and the like have been described as examples of the technique according to the present disclosure. The accompanying drawings and detailed descriptions have been provided to that end.

As such, the constituent elements indicated in the accompanying drawings and the detailed descriptions include not only constituent elements necessary to solve the technical problem, but also constituent elements not necessary to solve the problem but used to exemplify the above-described technique. Those unnecessary constituent elements being included in the accompanying drawings, the detailed description, and so on should therefore not be interpreted as meaning that the unnecessary constituent elements are in fact necessary.

Additionally, the foregoing embodiment is provided merely as one example of the technique according to the present disclosure, and thus many changes, substitutions, additions, omissions, and the like are possible within the scope of the claims or a scope equivalent thereto.

INDUSTRIAL APPLICABILITY

The present disclosure can be applied in a control method that suppresses an increase in a load on a server. Specifically, the present disclosure can be applied in a control method that controls a device that outputs a stimulus to a user.

REFERENCE SIGNS LIST 1, 1A, 1B, 2, 3 System
10, 10A, 10AA, 10B, 10BB, 10D, 10E, 90A, 90B Terminal
11, 11A, 11B, 11D Acceptor
12, 12A, 12B, 22, 22E Generator
13, 13A, 13B, 13D, 13E Controller
14, 14A, 14B Obtainer
15, 15A, 15B Presenter
20, 20A, 20B, 20D, 20E Server
21, 21A, 21B Provider
30 Sensor
41, 42 Image
50, 50A, 51, 51A, 52, 52A, 53, 53A, 54, 54A, 60, 61, 62, 70, 71, 72, 75, 76, 77, 80, 81, 82 Pattern
65 Operation point
85 Device
87 Lighting device
90 Control System
91 Bathtub
95 Image recording device
B Bedding
N Network
T, U User
V Vibration

The invention claimed is:

1. A control method executed by a computer to control a device that outputs a stimulus to a user, the control method comprising:
obtaining a stimulus start time that is a time when the device is to start outputting the stimulus;
determining whether or not the stimulus start time obtained satisfies a predetermined condition;
generating a pattern extended or contracted in a time direction from an initial pattern indicating a timewise change in an intensity of the stimulus when the stimulus start time obtained is determined to satisfy the predetermined condition; and
controlling the device to start outputting the stimulus at the stimulus start time and output the stimulus at the intensity indicated by the pattern generated.

2. The control method according to claim 1,
wherein the determining includes using, as the predetermined condition, a condition that the stimulus start time obtained is a time determined in advance as a time having a relatively high probability of being set as the stimulus start time by users of each of a plurality of devices each being the device.

3. The control method according to claim 1,
wherein the determining includes using, as the predetermined condition, a condition that a numerical value of a unit of minutes when the stimulus start time obtained is expressed in hour/minute/second format is 0, an integral multiple of 10, or an integral multiple of 15.

4. The control method according to claim 3,
wherein the determining further includes setting a range of an extension/contraction rate in accordance with the stimulus start time obtained,
the setting of the range of the extension/contraction rate includes:
setting a first range as the range of the extension/contraction rate when the numerical value of the unit of minutes is 0, when the stimulus start time is expressed in the hour/minute/second format;
setting a second range smaller than the first range as the range of the extension/contraction rate when the numerical value of the unit of minutes is 30, when the stimulus start time is expressed in the hour/minute/second format;
setting a third range smaller than the second range as the range of the extension/contraction rate when the numerical value of the unit of minutes is 15 or 45, when the stimulus start time is expressed in the hour/minute/second format; and
setting a fourth range smaller than the third range as the range of the extension/contraction rate when the numerical value of the unit of minutes is 10, 20, 40, or 50, when the stimulus start time is expressed in the hour/minute/second format, and
the generating of the pattern includes generating the pattern using an extension/contraction rate that is within the range of the extension/contraction rate set.

5. The control method according to claim 4,
wherein the generating of the pattern includes randomly selecting one extension/contraction rate among a plurality of extension/contraction rates that are within the range of the extension/contraction rate set, and generating the pattern using the one extension/contraction rate selected.

6. The control method according to claim 1,
wherein the initial pattern is a pattern in which the intensity of the stimulus stays constant or increases as time passes.

7. The control method according to claim 1,
wherein the initial pattern is a pattern in which:
(a) the intensity of the stimulus increases from 0 at the stimulus start time;
(b) the intensity of the stimulus increases and decreases in a range greater than 0 and less than a predetermined intensity until a predetermined length of time passes after the stimulus start time; and
(c) the intensity of the stimulus stays at the predetermined intensity after the predetermined length of time passes after the stimulus start time.

8. The control method according to claim 1,
wherein when an operation to stop the stimulus is accepted from the user, the device obtains, through communication with a server, information to be presented to the user, and the information obtained is presented to the user.

9. The control method according to claim 1,
wherein the stimulus is a stimulus prompting the user to wake up.

10. The control method according to claim 1,
wherein the stimulus includes any one of sound, light, temperature, wind, or vibration.

11. A non-transitory computer-readable recording medium having recorded thereon a program that causes a computer to execute the control method according to claim 1.

12. A control device that controls a device that outputs a stimulus to a user, the control device comprising:
a processor; and
a non-transitory computer-readable recording medium having recorded thereon a program,
wherein the program, when executed by the processor, causes the processor to perform:
obtaining a stimulus start time that is a time when the device is to start outputting the stimulus;
determining whether or not the stimulus start time obtained satisfies a predetermined condition, and generating a pattern extended or contracted in a time direction from an initial pattern indicating a timewise change in an intensity of the stimulus when the stimulus start time obtained is determined to satisfy the predetermined condition; and
controlling the device to start outputting the stimulus at the stimulus start time and output the stimulus at the intensity indicated by the pattern generated.

* * * * *